US010272050B2

(12) United States Patent
Farokhzad et al.

(10) Patent No.: US 10,272,050 B2
(45) Date of Patent: Apr. 30, 2019

(54) NANOPARTICLES AND METHODS OF USE

(71) Applicants: The Brigham and Women's Hospital, Inc., Boston, MA (US); President and Fellows of Harvard College, Cambridge, MA (US)

(72) Inventors: Omid C. Farokhzad, Waban, MA (US); Won Il Choi, Cambridge, MA (US); Ulrich von Andrian, Chestnut Hill, MA (US); Nazila Kamaly, Boston, MA (US)

(73) Assignees: The Brigham and Women's Hospital, Inc., Boston, MA (US); President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 15/519,052

(22) PCT Filed: Oct. 14, 2015

(86) PCT No.: PCT/US2015/055496
§ 371 (c)(1),
(2) Date: Apr. 13, 2017

(87) PCT Pub. No.: WO2016/061201
PCT Pub. Date: Apr. 21, 2016

(65) Prior Publication Data
US 2017/0216218 A1 Aug. 3, 2017

Related U.S. Application Data

(60) Provisional application No. 62/063,601, filed on Oct. 14, 2014.

(51) Int. Cl.
*A61K 9/51* (2006.01)
*A61K 38/18* (2006.01)
(Continued)

(52) U.S. Cl.
CPC .......... *A61K 9/5146* (2013.01); *A61K 9/0019* (2013.01); *A61K 9/5115* (2013.01);
(Continued)

(58) Field of Classification Search
None
See application file for complete search history.

(56) References Cited

U.S. PATENT DOCUMENTS

| | | | |
|---|---|---|---|
| 7,927,629 | B2 | 4/2011 | Simone et al. |
| 8,568,786 | B2 | 10/2013 | Simone et al. |

(Continued)

OTHER PUBLICATIONS

SY Kim, JC Ha, YM Lee. "Poly(ethylene oxide)-poly(propylene oxide)-poly(ethylene oxide) / poly(e-caprolactone) (PCL) amphiphilic block copolymeric nanospheres II. Thermo-responsive drug release behaviors." Journal of Controlled Release, vol. 65, 2000, pp. 345-358. (Year: 2000).*

(Continued)

*Primary Examiner* — Isaac Shomer
(74) *Attorney, Agent, or Firm* — Fish & Richardson P.C.; Vasity A. Ignatenko

(57) ABSTRACT

This disclosure relates to nanoparticles, compositions, methods of making, and methods of use thereof.

11 Claims, 12 Drawing Sheets

Specification includes a Sequence Listing.

(51) Int. Cl.

| | |
|---|---|
| ***A61K 38/20*** | (2006.01) |
| ***A61K 38/27*** | (2006.01) |
| ***A61K 38/28*** | (2006.01) |
| ***A61K 31/7088*** | (2006.01) |
| ***A61K 9/00*** | (2006.01) |
| *A61K 47/02* | (2006.01) |

(52) U.S. Cl.

CPC .......... *A61K 9/5153* (2013.01); *A61K 9/5192* (2013.01); *A61K 31/7088* (2013.01); *A61K 38/1816* (2013.01); *A61K 38/2013* (2013.01); *A61K 38/2066* (2013.01); *A61K 38/27* (2013.01); *A61K 38/28* (2013.01); *A61K 47/02* (2013.01); *Y02A 50/401* (2018.01); *Y02A 50/475* (2018.01); *Y02A 50/481* (2018.01); *Y10S 977/773* (2013.01); *Y10S 977/906* (2013.01)

(56) References Cited

U.S. PATENT DOCUMENTS

| | | | | |
|---|---|---|---|---|
| 2008/0081074 A1* | 4/2008 | Gu | A61K 9/5153 | 424/489 |
| 2009/0196937 A1* | 8/2009 | Tae | A61K 9/5146 | 424/501 |
| 2011/0268807 A1 | 11/2011 | Su et al. | | |
| 2012/0121718 A1* | 5/2012 | Lai | A61K 45/06 | 424/497 |
| 2013/0129829 A1* | 5/2013 | He | A61K 9/0004 | 424/493 |

OTHER PUBLICATIONS

JM Barichello, M Morishita, K Takayama, T Nagai. "Absorption of insulin from Pluronic F-127 gels following subcutaneous administration in rats." International Journal of Pharmaceutics, vol. 184, 1999, pp. 189-198. (Year: 1999).*

SH Choi, SH Lee, TG Park. "Temperature-Sensitive Pluronic/Poly(ethylenimine) Nanocapsules for Thermally Triggered Disruption of Intracellular Endosomal Compartment." Biomacromolecules, vol. 7, 2006, pp. 1864-1870. (Year: 2006).*

WI Choi, G Tae, YH Kim. "One pot, single phase synthesis of thermo-sensitive nano-carriers by photo-crosslinking of a diacrylated pluronic." Journal of Materials Chemistry, vol. 18, 2008, pp. 2769-2774. (Year: 2008).*

Alvarez et al., "Effects of PEGylation and immune complex formation on the pharmacokinetics and biodistribution of recombinant interleukin 10 in mice," Drug Metab. Dispos, 2012, 40: 360-373.

Bailon and Berthold, "Polyethylene glycol-conjugated pharmaceutical proteins," Pharm. Sci. Technol. Today, 1998, 1: 352-356.

Bakhru et al., "Oral delivery of proteins by biodegradable nanoparticles," Adv. Drug Deliv. Rev, Jun. 2013, 65: 811-821.

Barichello et al., "Absorption of insulin from Pluronic F-127 gels following subcutaneous administration in rats," International Journal of Pharmaceutics, 1999, 184: 189-198.

Baslé et al., "Protein chemical modification on endogenous amino acids," Chem. Biol, Mar. 2010, 17: 213-227.

Bi et al., "Solid lipid nanoparticles as insulin inhalation carriers for enhanced pulmonary delivery," J. Biomed. Nanotechnol, Feb. 2009, 5: 84-92.

Capiralla et al., "Identification of potent small-molecule inhibitors of STAT3 with anti-inflammatory properties in RAW 264.7 macrophages," FEBS J, 2012, 279: 3791-3799.

Carl et al., "Role of endogenous IL-10 in LPS-induced STAT3 activation and IL-1 receptor antagonist gene expression," J. Leukoc. Biol, 2004, 76: 735-742.

Chang et al., "Liquid perfluorochemical inhibits inducible nitric oxide synthase expression and nitric oxide formation in lipopolysaccharide-treated RAW 264.7 macrophages," J. Pharmacol. Sci, 2009, 111: 147-154.

Chappell et al., "Effect of insulin on cell cycle progression in MCF-7 breast cancer cells. Direct and potentiating influence," J. Biol. Chem, 2001, 276: 38023-38028.

Choi and Park, "G-CSF loaded biodegradable PLGA nanoparticles prepared by a single oil-in-water emulsion method," International Journal of Pharmaceutics, Mar. 2006, 311: 223-228.

Choi et al., "A Solvent-free Thermosponge Nanoparticle Platform for Efficient Delivery of Labile Proteins," Nano Letters, 2014, 14: 6449-6455.

Choi et al., "One pot, single phase synthesis of thermo-sensitive nano-carriers by photo-crosslinking of a diacrylated pluronic," J. Mater. Chem, 2008, 18: 2769-2774.

Choi et al., "Sustained release of human growth hormone from heparin-based hydrogel," Biomacromolecules, Jun. 2008, 9: 1698-1704.

Chung et al., "Strategies for non-invasive delivery of biologics," 2012, J. Drug Target, 20: 481-501.

Constantinides and Wasan, "Advances in lipid-based drug solubilization and targeting," Adv. Drug Deliv. Rev, 2004, 56: 1239-1240.

Dokka et al., "Interleukin-10-mediated inhibition of free radical generation in macrophages," Am. J. Physiol. Lung Cell Mol. Physiol, 2001, 280: L1196-L1202.

Errico et al., "Poly(hydroxyalkanoates)-based polymeric nanoparticles for drug delivery," J Biomed Biotechnol, 2009, 2009: 571702, 10 pages.

Harris and Chess, "Effect of pegylation on pharmaceuticals," Nat. Rev. Drug Discov, Mar. 2003, 2: 214-221.

Hasadsri et al., "Functional protein delivery into neurons using polymeric nanoparticles," J. Biol. Chem, Mar. 2009, 284: 6972-6981.

Heinemann, "Biosimilar insulins," Expert. Opin. Biol. Ther, 2012, 12: 1009-1016.

Hernández-Ledesma et al., "Antioxidant and anti-inflammatory properties of cancer preventive peptide lunasin in RAW 264.7 macrophages," Biochem. Biophys. Res. Commun, 2009, 390: 803-808.

Hinds and Kim, "Effects of PEG conjugation on insulin properties," Adv. Drug Deliv. Rev, Jun. 2002, 54: 505-530.

Huhn et al., "Pharmacokinetics and immunomodulatory properties of intravenously administered recombinant human interleukin-10 in healthy volunteers.," Blood, 1996, 87: 699-705.

International Preliminary Report on Patentability in International Application No. PCT/US2015/055496, dated Apr. 18, 2017.

Jain et al., "Polysialylated insulin: synthesis, characterization and biological activity in vivo," Biochim. Biophys. Acta, 2003, 1622: 42-49.

Jeong et al., "Thermosensitive sol-gel reversible hydrogels," Advanced Drug Delivery Reviews, 2002, 54: 37-51.

Johnson et al., "A month-long effect from a single injection of microencapsulated human growth hormone," Nat. Med, Jul. 1996, 2: 795-799.

Kamaly et al., "Targeted polymeric therapeutic nanoparticles: design, development and clinical translation," Chem. Soc. Rev, 2012, 41: 2971-3010.

Kamei et al., "Noninvasive insulin delivery: the great potential of cell-penetrating peptides," Ther. Deliv, Mar. 2013, 4: 315-326.

Kammona and Kiparissides, "Recent advances in nanocarrier-based mucosal delivery of biomolecules," J. Control. Release, Aug. 2012, 161: 781-794.

Kanaoka et al., "A novel and simple type of liposome carrier for recombinant interleukin-2," J. Pharm. Pharmacol, Marach 2001, 53: 295-302.

Keystone et al., "IL-10 as a therapeutic strategy in the treatment of rheumatoid arthritis," Rheum. Dis. Clin. North Am, Aug. 1998, 24: 629-639.

Kim et al., "Highly selective in-vivo imaging of tumor as an inflammation site by ROS detection using hydrocyanine-conjugated, functional nano-carriers," J. Control. Release, Dec. 2011, 156: 398-405.

Kim et al., "Pharmacodynamics of insulin in polyethylene glycol-coated liposomes," Int. J. Pharm, Mar. 1999, 180: 75-81.

Kobsa and Saltzman, "Bioengineering approaches to controlled protein delivery," Pediatr. Res, 2008, 63: 513-519.

(56) References Cited

OTHER PUBLICATIONS

Long et al., "Design of homogeneous, monopegylated erythropoietin analogs with preserved in vitro bioactivity," Exp. Hematol, Jun. 2006, 34: 697-704.
Martins et al., "Lipid-based colloidal carriers for peptide and protein delivery—liposomes versus lipid nanoparticles," Int. J. Nanomedicine, 2007, 2: 595-607.
Menon et al., "Effects of surfactants on the properties of PLGA nanoparticles," Journal of Biomedical Materials Research, Aug. 2012, 100A: 1998-2005.
Moghimi et al., "Reshaping the future of nanopharmaceuticals: ad iudicium," ACS Nano, 2011, 5: 8454-8458.
Orive et al., "Drug delivery in biotechnology: present and future," Curr. Opin. Biotechnol, 2003, 14: 659-664.
Pisal et al., "Delivery of therapeutic proteins," J. Pharm. Sci, Jun. 2010, 99: 2557-2575.
Pridgen et al., "Transepithelial transport of fc-targeted nanoparticles by the neonatal fc receptor for oral delivery," Sci. Transl. Med, Nov. 2013, 5: 213ra167.
Schmidt, "Recombinant expression systems in the pharmaceutical industry," Appl. Microbiol. Biotechnol, Sep. 2004, 65: 363-372.
Schwarz et al., "In vivo effects of interleukin-10 on contact hypersensitivity and delayed-type hypersensitivity reactions," J. Invest. Dermatol, Aug. 1994, 103: 211-216.
Sinclair and Elliott, "Glycoengineering: the effect of glycosylation on the properties of therapeutic proteins," J. Pharm. Sci, Aug. 2005, 94: 1626-1635.
Smola et al., "Nanocarriers as pulmonary drug delivery systems to treat and to diagnose respiratory and non respiratory diseases," Int. J. Nanomedicine, 2008, 3: 1-19.
Soppimath et al., "Biodegradable polymeric nanoparticles as drug delivery devices," J. Control. Release, 2001, 70: 1-20.
Tabas and Glass, "Anti-inflammatory therapy in chronic disease: challenges and opportunities," Science, Jan. 2013, 339: 166-172.
Utama et al., "Synthesis of hollow polymeric nanoparticles for protein delivery via inverse miniemulsion periphery RAFT polymerization," Chem. Commun, 2012, 48: 11103-11105.
Wang et al., "Pluronic F127 gel effectively controls the burst release of drug from PLGA microspheres," Pharmazie, 2006, 61: 367-368.
Yan et al., "A novel intracellular protein delivery platform based on single-protein nanocapsules," Nat. Nanotechnol, Jan. 2010, 5: 48-53.
Yang et al., "Biodegradable Nanoparticles Composed Entirely of Safe Materials that Rapidly Penetrate Human Mucus," Angewandte Chemie, Mar. 2011, 50: 2597-2600.
Zhang et al., "Discussion about several potential drawbacks of PEGylated therapeutic proteins," Biol. Pharm. Bull, 2014, 37: 335-339.
Koppolu B. et al., "Development of multiple-layer polymeric particles for targeted and controlled drug delivery," Nanomedicine 6(2): 355-361 (Apr. 2010).
International Search Report and Written Opinion dated Feb. 2, 2016 in international application No. PCT/US15/55496, 18 pgs.
Barichello et al., "Encapsulation of Hydrophilic and Lipophilic Drugs in PLGA Nanoparticles by the Nanoprecipitation Method," Drug Development and Industrial Pharmacy, 1999, 25: 471-476.

* cited by examiner

NANOPARTICLES AND METHODS OF USE

CLAIM OF PRIORITY

This application is a § 371 National Stage Application of PCT/US2015/055496, filed Oct. 14, 2015, which claims the benefit of U.S. Provisional Application No. 62/063,601, filed Oct. 14, 2014. The entire contents of the foregoing are hereby incorporated by reference.

STATEMENT AS TO FEDERALLY SPONSORED RESEARCH

This invention was made with Government support under Grant No. HHSN268201000045C, awarded by the National Institutes of Health. The Government has certain rights in the invention.

TECHNICAL FIELD

This invention relates to nanoparticles, compositions, methods of making, and methods of use thereof.

BACKGROUND

Since the discovery of insulin in the last century, there has been an effort to develop improved methods for the delivery of biomolecules such as proteins to patients via, e.g., pulmonary, nasal, subcutaneous, and oral routes. The main avenues of research in the field of biomolecule delivery include chemical modification of proteins with sugars, amino acids, or pegylation; or the encapsulation, entrapment, or incorporation of proteins within carriers. Nanotechnology has played a role in the design of optimal delivery carriers for biomolecules, with polymeric nanoparticles being effective platforms for, e.g., protein delivery due to the possibility of fine-tuning their biophysicochemical properties, in addition to their ability to protect and release proteins in a controlled manner. However, the clinical translation of protein drugs and protein-delivering nanomedicines has been hindered due to difficulties in the development and manufacturing of protein-based therapeutics that must be overcome to achieve clinical translation. Limitations such as synthetic chemical coupling and formulation parameters such as homogenization, sonication, extrusion, and exposure to solvents lead to the inactivation of biomolecules.

SUMMARY

The present invention provides methods and compositions of nanoparticles comprising a core and an outer layer of a polymer. In one embodiment, the nanoparticles can absorb and release biomolecules such as therapeutic proteins depending on the temperature and the differing behavior and characteristics of the polymer in aqueous media. The nanoparticles can self-assemble via a simple single-step nanoprecipitation process. In addition, characteristics of drug absorption and drug release can be tuned, e.g., the core polymer can exhibit a positive or negative charge, thus allowing for preferential absorption and subsequent release of negatively or positively charged biomolecules, such as proteins, respectively. The nanoparticles can also allow for the efficient delivery of labile biomolecules using an organic-solvent-free polymer thermoexpansion mechanism with clinical potential, capable of effectively delivering a biomolecule such as a therapeutic protein, e.g., interleukin-10, in a sustained manner with minimal or no loss of bioactivity, and an improved half-life and in vivo efficacy compared with administration of the therapeutic protein alone.

Provided herein is a composition comprising: a nanoparticle comprising a core and an outer layer comprising a polymer surrounding the core; and a biomolecule selectively encapsulated in the outer layer of the nanoparticle; wherein the polymer exhibits temperature-dependent conformational changes that change the size of the nanoparticle by an amount in the range from about 5% to about 500% in an aqueous medium substantially free of organic solvent.

Also provided herein is a composition comprising: a nanoparticle comprising a core and an outer layer comprising a polymer surrounding the core; and a biomolecule selectively encapsulated in the outer layer of the nanoparticle; wherein the polymer exhibits temperature-dependent conformational changes that change the size of the nanoparticle by an amount sufficient to provide for encapsulation of the biomolecule from an aqueous medium substantially free of organic solvent.

Also provided herein is a composition comprising: a nanoparticle comprising a core and an outer layer comprising a polymer surrounding the core; and a biomolecule selectively encapsulated in the outer layer of the nanoparticle; wherein the polymer exhibits temperature-dependent conformational changes that change the size of the nanoparticle by an amount sufficient to provide for encapsulation of the biomolecule from an aqueous medium substantially free of organic solvent.

Provided herein is a method comprising: (a) preparing a composition comprising a nanoparticle comprising a core and an outer layer comprising a polymer surrounding the core; an aqueous medium substantially free of organic solvent; and a biomolecule dissolved or suspended in the aqueous medium; (b) subjecting the composition to a first temperature at which the polymer expands to allow entry of the biomolecule into the outer layer; and (c) subjecting the composition to a second temperature at which the polymer contracts to encapsulate the biomolecule in the outer layer.

Provided is a method of treating a cancer in a subject in need thereof, comprising administering to the subject a therapeutically effective amount of a composition described herein.

Also provided is a method of treating an anemia in a subject in need thereof, comprising administering to the subject a therapeutically effective amount of a composition described herein.

Also provided is a method of treating diabetes in a subject in need thereof, comprising administering to the subject a therapeutically effective amount of a composition described herein.

Also provided is a method of treating a disease or condition beneficially treated by administration of a growth hormone in a subject in need thereof, comprising administering to the subject a therapeutically effective amount of a composition described herein.

Also provided is a method of treating an inflammatory disease or condition in a subject in need thereof, comprising administering to the subject a therapeutically effective amount of a composition described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the description and drawings, and from the claims.

BRIEF DESCRIPTION OF THE DRAWINGS

FIG. 1*a* shows hydrodynamic diameters and FIG. 1*b* shows surface charges (ζ(zeta)-potential) of thermosponge nanoparticles (TNPs) using PLGA or PLA as a core and Pluronic F127 as a shell at 25° C. (mean±SD, n=3).

FIG. 2*a* shows PLGA-based and FIG. 2*b* shows PLA-based thermosponge nanoparticles in PBS (pH 7.4) containing 10% fetal bovine serum (FBS) in a shaking incubator at 100 rpm and 37° C. FIG. 2*c* shows PLGA-based and FIG. 2*d* shows PLA-based thermosponge nanoparticles before and after lyophilization without the use of a cryo-protectant (n=3). N/A: not available due to aggregation.

FIG. 4*a*: Hydrodynamic diameters, and FIG. 4*b*: surface charges of TNPs and therapeutic protein-loaded TNPs. FIG. 4*c*: Representative TEM image of TNPs. The scale bar is 500 nm. Inset is a high-magnification image with the scale bar representing 50 nm. FIG. 4*d*: Swelling and deswelling behavior of TNPs in response to temperature changes. FIG. 4*e*: Loading contents (wt %) of therapeutic proteins (Bars from left to right: IL-10, EPO, insulin, and hGH) into negatively charged or positively charged TNPs. FIG. 4*f*: In vitro cumulative release patterns of therapeutic proteins from TNPs in PBS buffer at 100 rpm and 37° C., analyzed by ELISA (mean±SD, n=3).

FIG. 6*a* shows TNP preparation by a one-step nanoprecipitation method. FIG. 6*b* shows a solvent-free method of protein-loading TNPs for efficient delivery of labile therapeutic protein drugs. TNPs can be efficiently loaded with desired proteins without organic solvents, due to the combination of the swelling behavior of the Plutonic shell of TNPs at 4° C. and the electrostatic interactions between the absorbed proteins and the PLA core of nanoparticles.

FIG. 8*a* shows intracellular ROS production in RAW 264.7 macrophage cells by LPS stimulation, measured using $DCFH_2$-DA dye. FIG. 8*b* shows cell viability in LPS concentration ranging from 100 to 1000 ng/mL for 4 h and 24 h (n=3).

FIG. 9*a*: Inhibitory effects on ROS production by IL-10 at various concentrations (1-100 ng/mL). Intracellular ROS generated from RAW 264.7 macrophage cells by LPS stimulation was measured using a ROS detection reagent. Bioactivity analysis of the inhibitory effects of native IL-10, released IL-10, and loaded IL-10 on ROS production by pre-treatment (FIG. 9*b*) and by post-treatment (FIG. 9*c*) of IL-10 (n=3, # p>0.05). FIG. 9*d*: Relative mRNA expression of TNF-α, IL-12, and sIL-1Ra after LPS treatment (500 ng/mL) for 4 h, followed by treatment with IL-10 (native IL-10 or released IL-10 at 20 ng/mL) for 2 h at 37° C. (n=3, # p>0.05). FIG. 9*e*: Western blots were performed to analyze the bioactivity of IL-10 released from TNPs after treatment with IL-10 (native IL-10 or released IL-10 at 20 ng/mL) for 24 h at 37° C. #1: Control, #2: native IL-10, and #3: released IL-10. FIG. 9*f*: Bioactivity analysis of native insulin and released insulin (10 nM) on the improved proliferation effect of insulin-dose-dependent human breast cancer cell line MCF-7 (n=3, # p>0.05).

FIG. 12*a*: Therapeutic efficacy of IL-10 and TNPs on ear swelling in a mouse model of allergic contact dermatitis (ACD) at 100 μg IL-10/kg dose via i.v. administration. FIG. 12*b*: Representative histological images of DNFB-treated ears from IL-10 and IL-10-loaded TNP groups. FIG. 12*c*: Total neutrophils (CD11b+, Ly-6Ghigh) in skin at 36 h upon acetone or DNFB challenge. All data are expressed as mean±SEM of n=4 to 7 per group. * p<0.05 for saline vs. treatment.

DETAILED DESCRIPTION

Figure 1:
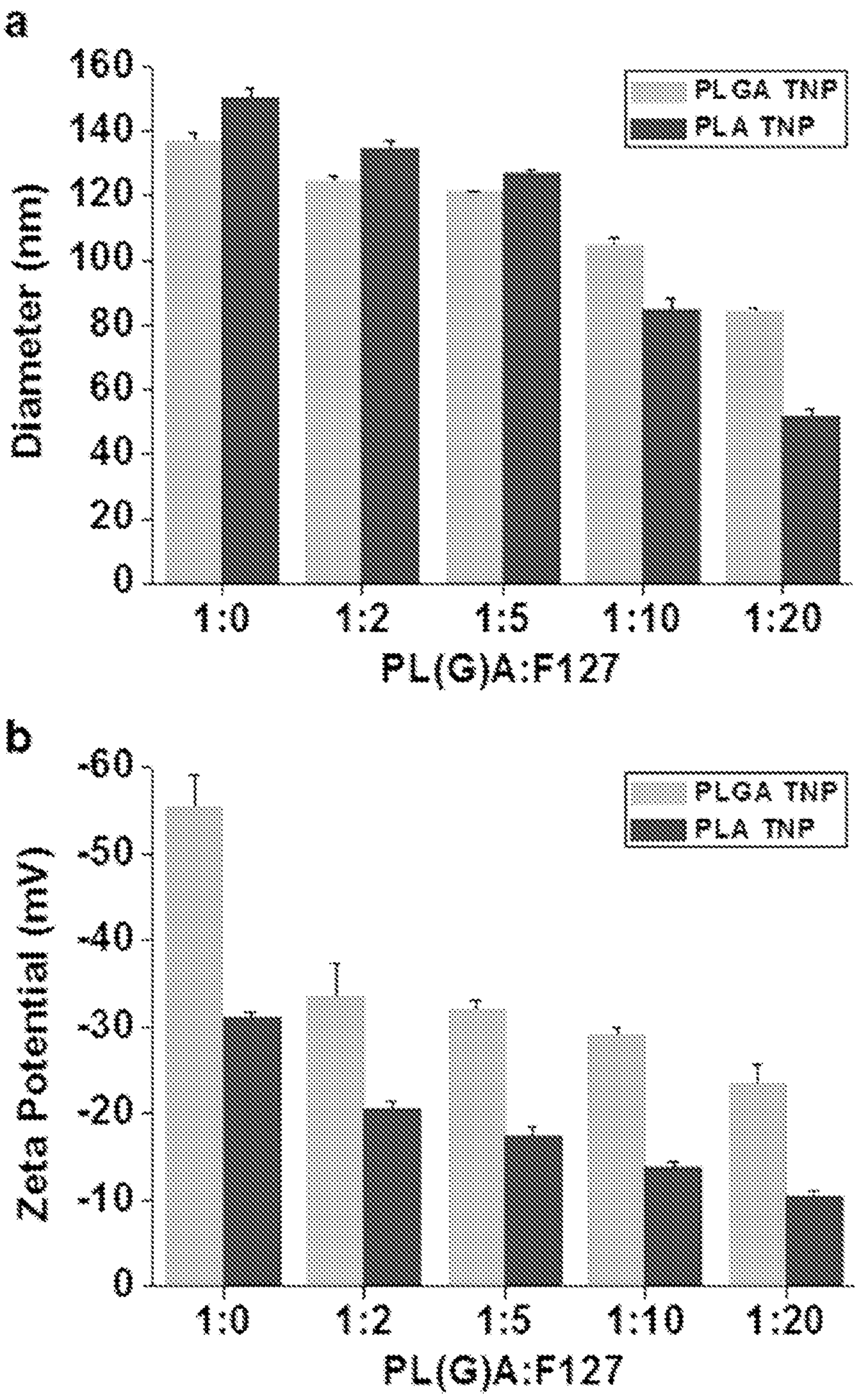
FIG. 1 shows the size and surface charges of nanoparticles.

The current disclosure provides the preparation and use of nanoparticles comprising a core and an outer layer of a polymer. The nanoparticles may be synthesized by nanoprecipitation methods in a simple manner, without requiring detergents or sonication, and can be placed into an aqueous, organic solvent-free environment prior to the introduction of a payload. Further, the size and/or density of the nanoparticles produced by this method may result in an enhanced efficacy of docking and release of the payload from the nanoparticle. This platform takes advantage of the nature of the polymer comprising the outer layer to encapsulate a payload and to be able subsequently to release it. By removing organic solvents before introduction of a payload, this approach allows for delivery of payloads that may adversely react with or be deactivated by organic solvents.

In the present description, it is appreciated that certain features described herein, which are, for clarity, described in the context of separate embodiments, can also be provided in combination in a single embodiment. Conversely, various features described herein which are, for brevity, described in the context of a single embodiment, can also be provided separately or in any suitable subcombination.

Although methods and materials similar or equivalent to those described herein can be used in the practice or testing of the present invention, suitable methods and materials are described below. In addition, the materials, methods and examples are illustrative only and not intended to be limiting.

Definitions

Unless defined otherwise, all technical and scientific terms used herein have the same meaning as is commonly understood by one of ordinary skill in the art to which this disclosure belongs.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

As used herein, a "poloxamer" is a polymer composed of a central hydrophobic chain of poly(propylene oxide) flanked by two hydrophilic chains of poly(ethylene oxide).

The term "nanoparticle" as used herein refers to a particle having a size from about 1 nm to about 1000 nm.

The term "nanoparticle size" as used herein refers to the median size in a distribution of nanoparticles. The median size is determined from the average linear dimension of individual nanoparticles, for example, the diameter of a spherical nanoparticle. Size may be determined by any number of methods in the art, including dynamic light scattering (DLS) and transmission electron microscopy (TEM) techniques.

As used herein, "thermosponge nanoparticle" refers to nanoparticles having an outer layer comprising a polymer that thermally expands and contracts to provide for encapsulation of a payload into the outer layer of the nanoparticle.

References to a composition described and disclosed herein are considered to include the free acid, the free base, and all addition salts. The compositions may also form inner salts or zwitterions when a free carboxy and a basic amino group are present concurrently. The term "pharmaceutically acceptable salt" refers to salts which possess toxicity profiles within a range that affords utility in pharmaceutical applications. In general the useful properties of the compositions described herein do not depend on whether the composition is or is not in a salt form, so unless clearly indicated otherwise (such as specifying that the composition should be in "free base" or "free acid" form), reference in the specification to a composition should be understood as including salt forms of the composition, whether or not this is explicitly stated. Preparation and selection of suitable salt forms is described in Stahl et al., *Handbook of Pharmaceutical Salts: Properties, Selection, and Use*, Wiley-VCH 2002.

When in the solid state, the compositions described herein and salts thereof may occur in various forms and may, e.g., take the form of solvates, including hydrates. In general, the useful properties of the compositions described herein do not depend on whether the composition or salt thereof is or is in a particular solid state form, such as a polymorph or solvate, so unless clearly indicated otherwise reference in the specification to compositions and salts should be understood as encompassing any solid state form of the composition, whether or not this is explicitly stated.

Compositions provided herein can also include all isotopes of atoms occurring in the intermediates or final compositions. Isotopes include those atoms having the same atomic number but different mass numbers. For example, isotopes of hydrogen include tritium and deuterium.

As used herein, "substantially free of organic solvents" refers to compositions which are mostly or entirely free of organic solvents. For example, an aqueous mixture substantially free of organic solvents is an aqueous mixture which has been subjected to processes that have removed most or all organic solvents from the mixture. In some embodiments, a composition substantially free of organic solvents can comprise about 5% or less, about 2% or less, about 1% or less, about 0.5% or less, 0.1% or less 0.05% or less, or about 0.01% or less by weight of organic solvents. In some embodiments, a composition substantially free of organic solvents can comprise about 5%, about 2%, about 1%, 0.5%, about 0.1%, about 0.05%, or about 0.01% organic solvents. In some embodiments, a composition substantially free of organic solvents can comprise aqueous solutions comprising a pharmaceutically acceptable buffer. In some embodiments, a composition substantially free of organic solvents can comprise aqueous solutions comprising a pharmaceutically acceptable salt. Common pharmaceutically acceptable buffers include acetate (acetic acid and sodium acetate), citrate (citric acid and sodium citrate), and phosphate (sodium phosphate and disodium phosphate) buffers. Pharmaceutically acceptable salt solutions include dilute saline solutions. For example, the composition can be in a pH-buffered phosphate solution or a saline solution. In some embodiments, a composition substantially free of organic solvents is a composition in water. In some embodiments, a composition substantially free of organic solvents can be free of salts.

Abbreviations

The following abbreviations may be used in the present disclosure.

AUMC=area under the first moment curve, AUC=area under the serum concentration-time curve, BSA=bovine serum albumin, $DCFH_2$-DA=2',7'-dichlorofluorescin diacetate, DNFB=2,4-dinitro-1-fluorobenzene, dNTP=deoxynucleotide mixture, ELISA=enzyme-linked immunosorbent assay, EPO=erythropoietin, FBS=fetal bovine serum, hGH=human growth hormone, IL-10=interleukin-10, IL-12=interleukin-12, LPS=lipopolysaccharide, mAb=monoclonal antibody, mRNA=messenger ribonucleic acid, MRT=mean residence time, MWCO=molecular weight cutoff, PCR=polymerase chain reaction, PBS=phosphate-buffered saline, PLA=poly (lactic acid), PLGA=poly(lactic-co-glycolic acid), rpm=revolutions per minute, ROS=reactive oxygen species, SEM=standard error of the mean, TBST=Tris-buffered saline and Tween 20 buffer, TEM=transmission electron microscopy, TNP=thermosponge nanoparticle, Vss=volume of distribution at steady state.

Nanoparticles

The present disclosure provides a nanoparticle comprising a core and an outer layer of a polymer. Under thermal conditions, the outer layer polymer can be used to encapsulate and subsequently to deliver a payload.

The core of the nanoparticle can comprise a variety of materials. In some embodiments, the core comprises an organic material. In some embodiments, the organic material comprises a polymer. Non-limiting exemplary polymers include polymer systems that are approved for use in humans, e.g., poly(glycolic acid), poly(lactic acid), poly (caprolactone), poly(lactide-co-glycolide), poly(ortho ester)

II, poly(alkyl cyanoacrylate), desaminotyrosyl octyl ester, polyphosphoesters, polyester amides, polyurethanes, chitosan, and lipids. Other non-limiting examples of polymers that the core can comprise include: Acrylates copolymer; Acrylic acid-isooctyl acrylate copolymer; Ammonio methacrylate copolymer O; Ammonio methacrylate copolymer type A O; Ammonio methacrylate copolymer type B O; Butyl ester of vinyl methyl ether/maleic anhydride copolymer (125,000 molecular weight); Carbomer homopolymer type A (allyl pentaerythritol crosslinked) O; Carbomer homopolymer type B (allyl sucrose crosslinked) T; Cellulosic polymers O; Dimethylaminoethyl methacrylate-butyl methacrylate-methyl methacrylate copolymer O; Dimethylsiloxane/methylvinylsiloxane copolymer I; Divinylbenzene styrene copolymer OPH; Ethyl acrylate-methacrylic acid copolymer O; Ethyl acrylate and methyl methacrylate copolymer (2:1; 750,000 molecular weight) O; Ethylene vinyl acetate copolymer I; Ethylene-propylene copolymer; Ethylene-vinyl acetate copolymer (28% vinyl acetate) V; Glycerin polymer solution i-137 O; Glycerin polymer solution im-137 O; Hydrogel polymer V; Ink/polyethylene terephthalate/aluminum/polyethylene/sodium polymethacrylate/ethylene vinyl acetate copolymer; Isooctyl acrylate/acrylamide/vinyl acetate copolymer; Kollidon® VA 64 polymer O; Methacrylic acid-ethyl acrylate copolymer (1:1) type A O; Methacrylic acid-methyl methacrylate copolymer (1:1) O; Methacrylic acid-methyl methacrylate copolymer (1:2) O; Methacrylic acid copolymer O; Methacrylic acid copolymer type A O; Methacrylic acid copolymer type B O; Methacrylic acid copolymer type C O; Octadecene-1/maleic acid copolymer T; PEG-22 methyl ether/dodecyl glycol copolymer T; PEG-45/dodecyl glycol copolymer T; Polyester polyamine copolymer; Poly(ethylene glycol) 1,000 O, R, RP, and V; Poly(ethylene glycol) 1,450 O, T, and U; Poly (ethylene glycol) 1,500 O and T; Poly(ethylene glycol) 1,540 D and R; Poly(ethylene glycol) 200 IM, O, and T; Poly(ethylene glycol) 20,000 O; Poly(ethylene glycol) 200,000 O; Poly(ethylene glycol) 2,000,000; Poly(ethylene glycol) 300 IV, IM, OPH, and T; Poly(ethylene glycol) 300-1,600 O; Poly(ethylene glycol) 300-1,600 T; Poly(ethylene glycol) 3,350; Poly(ethylene glycol) 3,500 O; Poly(ethylene glycol) 400 IV, N, OPH, O, R, T, and V; Poly(ethylene glycol) 4,000 IA, IL, IM, O, R, SL, and V; Poly(ethylene glycol) 4,500 O; Poly(ethylene glycol) 540 T; Poly(ethylene glycol) 600 IV, O, and T; Poly(ethylene glycol) 6,000 O, R, T, and V; Poly(ethylene glycol) 7,000 O; Poly(ethylene glycol) 7,000,000 O; Poly(ethylene glycol) 800 O; Poly (ethylene glycol) 8,000 O, OPH, T, and V; Poly(ethylene glycol) 900 T; Polyvinyl chloride-polyvinyl acetate copolymer TD; Povidone acrylate copolymer T; Povidone/eicosene copolymer T; Polyoxy(methyl-1,2-ethanediyl), alpha-hydro-omega-hydroxy-, polymer with 1,1'-methylenebis[4-isocyanatocyclohexane] copolymer (Ppg-12/SMDI); Polyvinyl methyl ether/maleic acid copolymer (PVM/MA) D, paste 9011169; Styrene/isoprene/styrene block copolymer T; and Vinyl acetate-crotonic acid copolymer O, sustained-action capsule.

In some embodiments, the core comprises a hydrophobic polymer. Non-limiting examples of hydrophobic polymers include, but are not limited to: polylactic acid (PLA), polypropylene oxide, poly(lactide-co-glycolide) (PLGA), poly(epsilon-caprolactone), poly(ethylethylene), polybutadiene, polyglycolide, polymethylacrylate, polyvinylbutylether, polystyrene, polycyclopentadienyl-methylnorbornene, polyethylenepropylene, polyethylethylene, polyisobutylene, polysiloxane, a polymer of any of the following: methyl acrylate, ethyl acrylate, propyl acrylate, n-butyl acrylate, isobutyl acrylate, 2-ethyl acrylate, t-butyl acrylate, methacrylates (e.g., ethyl methacrylate, n-butyl methacrylate, and isobutyl methacrylate), acrylonitriles, methacrylonitrile, vinyls (e.g., vinyl acetate, vinylversatate, vinylpropionate, vinylformamide, vinylacetamide, vinylpyridines, and vinyllimidazole), aminoalkyls (e.g., aminoalkylacrylates, aminoalkylsmethacrylates, aminoalkyl(meth)acrylamides), styrenes, and lactic acids.

In some embodiments, the core comprises an amphiphilic polymer. Amphiphilic polymers contain a molecular structure containing one or more repeating units (monomers) connected by covalent bonds and the overall structure includes both hydrophilic (polar) and lipophilic (apolar) properties, e.g., at opposite ends of the molecule. In some embodiments, the amphiphilic polymers are copolymers containing a first hydrophilic polymer and a first hydrophobic polymer. Several methods are known in the art for identifying an amphiphilic polymer. For example, an amphiphilic polymer (e.g., an amphiphilic copolymer) can be identified by its ability to form micelles in an aqueous solvent and/or Langmuir Blodgett films.

In some embodiments, the amphiphilic polymer (e.g., an amphiphilic copolymer) contains a polymer selected from the group of: polyethylene glycol (PEG), polyethylene oxide, polyethyleneimine, diethyleneglycol, triethyleneglycol, polyalkalene glycol, polyalkyline okxide, polyvinyl alcohol, sodium polyphosphate, polyvinylpyrrolidone, polyvinylmethylether, polymethyloxazoline, polyethyloxazoline, polyhydroxypropyl-oxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyglycerine, polyaspartamide, hyaluronic acid, polyoxyethlene-polyoxypropylene copolymer (poloxamer), a polymer of any of lecithin or carboxylic acids (e.g., acrylic acid, methacrylic acid, itaconic acid, and maleic acid), polyoxyethylenes, polyethyleneoxide, and unsaturated ethylenic monocarboxylic acids. In some embodiments, the amphiphilic polymer contains a polymer selected from the group of: polylactic acid (PLA), polypropylene oxide, poly(lactide-co-glycolide) (PLGA), poly(epsilon-caprolactone), poly(ethylethylene), polybutadiene, polyglycolide, polymethylacrylate, polyvinylbutylether, polystyrene, polycyclopentadienylmethylnorbornene, polyethylenepropylene, polyethylethylene, polyisobutylene, polysiloxane, and a polymer of any of the following: methyl acrylate, ethyl acrylate, propyl acrylate, n-butyl acrylate, isobutyl acrylate, 2-ethyl acrylate, t-butyl acrylate, methacrylates (e.g., ethyl methacrylate, n-butyl methacrylate, and isobutyl methacrylate), acrylonitriles, methacrylonitrile, vinyls (e.g., vinyl acetate, vinylversatate, vinylpropionate, vinylformamide, vinylacetamide, vinylpyridines, and vinyllimidazole), aminoalkyls (e.g., aminoalkylacrylates, aminoalkylsmethacrylates, and aminoalkyl(meth)acrylamides), styrenes, and lactic acids.

In some embodiments, the amphiphilic polymer contains PLA-PEG, PLGA-PEG (e.g., the amphiphilic polymer is PLGA-PEG), polystyreneblock-polyethyleneoxide, polybutylacrylate-b-polyacrylic acid, or polybutylmethacrylate-b-polyethyleneoxide. Additional examples of amphiphilic copolymers are described in U.S. Patent Application Publication No. 2004/0091546 (incorporated herein by reference in its entirety). Additional examples of amphiphilic polymers (e.g., amphiphilic copolymers) are known in the art.

In some embodiments, the core comprises a polymer comprising an aliphatic polyester polymer, e.g., polycaprolactone (PCL), polybutylene succinate (PBS), or a polyhydroxylalkanoate (PHA), such as polyhydroxybutyrate. Other examples include polylactic acid (PLA) and polyglycolic acid (PGA). In some embodiments, the aliphatic polyester polymer is selected from polylactic acids, polyglycolic acids, and copolymers of lactic acid and glycolic acid (PLGA). A copolymer of lactic acid and glycolic acid can comprise a range of ratios of lactic acid to glycolic acid monomers, for example, from about 1:9 to about 9:1, from about 1:4 to about 4:1, from about 3:7 to about 7:3, or from about 3:2 to about 2:3. In some embodiments, the ratio of lactic acid to glycolic acid monomers can be about 1:9; about 1:8; about 1:7; about 1:6; about 1:5; about 1:4; about 3:7; about 2:3; about 1:1; about 3:2; about 7:3; about 4:1; about 5:1; about 6:1; about 7:1; about 8:1; or about 9:1. In some embodiments, the core can consist essentially of, or consist of such materials.

In some embodiments, the core comprises an inorganic material. For example, the inorganic material can be a nanoparticle comprising gold, silver, copper, zinc, titanium, iron, platinum, palladium, gadolinium, lithium, and/or silicon. Other non-limiting examples of inorganic materials include metal oxides (e.g., iron oxide), silica, and carbon (e.g., carbon nanospheres).

A core may comprise one or more materials. In a non-limiting example, the core can consist essentially of a gold nanoparticle. In another example, the core can comprise a mixture of copper and zinc nanoparticles.

In some embodiments, the core (and particularly the surface of the core) can have an electrical charge, e.g., a negative or a positive charge. In some embodiments, a net negative charge is provided by acidic groups (e.g. carboxylate, phosphate or sulfonate groups) included in a material included in the core. In some embodiments, a net positive charge is provided by basic groups (e.g. amine or ammonium groups) included in a material included in the core. In a non-limiting example, a core comprising mostly PLGA-COOH would have a net negative charge on its surface as measured by ζ (zeta)-potential, while a core comprising mostly PLA-$NH_2$ would have a net positive charge. The electrical charge can allow for the efficient and high loading of a complementarily charged payload. For example, a negatively charged core can afford a high loading of a positively charged payload, e.g., a protein, such as mouse interleukin-10 or human erythropoietin, having an isoelectric point (pI) above about 7. In another non-limiting example, a positively charged core can offer a high loading of a negatively charged payload, e.g., a protein, such as human insulin or human growth hormone, having a pI below about 7.

The outer layer comprises a polymer that exhibits temperature-dependent conformational changes that change the size of the nanoparticle by an amount sufficient to provide for encapsulation of the biomolecule from an aqueous medium substantially free of organic solvent. For instance, the polymer can exhibit temperature-dependent conformational changes that change the size of the nanoparticle by an amount in the range from about 5% to about 500% in an aqueous medium substantially free of organic solvent. In some embodiments, the temperature-dependent conformational changes can change the size of the nanoparticle by an amount in the range from about 50% to about 400%, from about 100% to about 350%, from about 150% to about 350%, from about 200% to about 350%, or from about 200% to about 300% in an aqueous medium substantially free of organic solvent. In some embodiments, the outer layer can comprise a polymer that is a poly(acrylic acid-co-acrylamide), an elastin-like oligo- and polypeptide, poly(N-ethyl oxazoline) (PEtOx), poly(N-vinyl caprolactam) (PVCa), poly(methyl vinyl ether) (PMVE), poly(N-alkylacrylamide), poly (N-isopropylacrylamide) (PNIPAM), or an oligoethylene glycol-derived acrylate, methacrylate, acrylamide, or methacrylamide. The polymer can be linear, branched, or crosslinked. The temperature-dependent conformational changes can occur over a temperature range from about 0° C. to about 100° C., for example, a temperature range of from about 0° C. to about 50° C., from about 0° C. to about 40° C., from about 4° C. to about 40° C., from about 0° C. to about 37° C., or from about 4° C. to about 37° C.

The temperature-dependent conformational changes can first involve expansion of the outer layer of the nanoparticle to allow entry of a biomolecule into the outer layer of the nanoparticle then contraction of the outer layer to encapsulate the biomolecule in the outer layer. The temperature is in a range of from about 0° C. to about 100° C. In some embodiments, the temperature is in a range of from about 0° C. to about 40° C. The expansion of the outer layer of the nanoparticle to allow entry of the biomolecule can occur, e.g., at a temperature in the range from about 0° C. to about 20° C., from about 0° C. to about 15° C., from about 0° C. to about 10° C., from about 0° C. to about 5° C., e.g., at about 0° C., 1° C., 2° C., 3° C., 4° C. or 5° C. The contraction of the outer layer of the nanoparticle to encapsulate the biomolecule can occur, e.g., at a temperature in the range from about 10° C. to about 50° C., from about 20° C. to about 50° C., from about 30° C. to about 50° C., from about 15° C. to about 45° C., from about 25° C. to about 45° C., from about 35° C. to about 45° C., from about 30° C. to about 40° C., or from about 35° C. to about 40° C., e.g., at about 35° C., 36° C., 37° C., 38° C., 39° C. or 40° C. For example, the temperature can be at about 4° C. to allow entry of a biomolecule into the nanoparticle, then be raised to about 37° C. to allow encapsulation of the biomolecule. The process can be used to encapsulate the biomolecule selectively in the outer layer of the nanoparticle so that the core of the nanoparticle can be substantially free of the biomolecule. For example, about 80% or more, about 85% or more, about 90% or more, about 95% or more, about 98% or more, about 99% or more, or about 100% of the of the biomolecule can be encapsulated in the outer layer of the nanoparticle.

The molecular weight of the polymer found in the outer layer can vary in a range from about 6,500 to about 13,000 daltons. As used herein, the molecular weight of a polymer is $M_w$, the mass average molar mass, or the weight average molecular weight of all polymer chains in the sample. For example, the molecular weight can be about 6,700 daltons.

In some embodiments, the outer layer comprises a polymer that is a poloxamer. In some embodiments, the outer layer comprises a polymer having the formula:

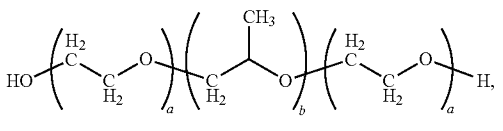

wherein each a can be the same or different. In some embodiments, a is an integer in the range of about 2 to about 200. In some embodiments, a is an integer in the range of about 10 to about 150 or about 10 to about 100. In some embodiments a can be about 12, about 64, about 80, about 101, or about 141. In some embodiments, b is an integer in the range of about 10 to about 100. In some embodiments, b can be in the range of about 10 to about 80, or about 20 to about 80. In some embodiments, b is an integer in the range of about 15 to about 70. For example, b can be about 20, about 27, about 37, about 44, or about 56.

Some brands of poloxamers include Pluronic® (e.g., Pluronic® F127, F68, F87, F88, F98, F108, P105, L35, L44, and L64), Synperonic®, and Kolliphor®. In some embodiments, the molecular mass of the poly(propylene oxide) central chain is in a range from about 3000 g/mol to about 5000 g/mol. In some embodiments, the molecular mass of the poly(propylene oxide) central chain is in a range from about 3600 g/mol to about 4000 g/mol. In some embodiments, a poloxamer can have a molecular mass of the poly(propylene oxide) central chain of about 3600 g/mol. In some embodiments, a poloxamer can have a molecular mass of the poly(propylene oxide) central chain of about 4000 g/mol. In some embodiments, the poloxamer comprises a poly(ethylene oxide) content in a range from about 60% to about 80% by weight. For example, the poloxamer can comprise a poly(ethylene oxide) content of about 60%, about 65%, about 70%, about 75%, or about 80% by weight, or the poly(ethylene oxide) content can fall within a range between any two of these values. In some embodiments, a poloxamer can comprise a poly(ethylene oxide) content of about 70%. In some embodiments, the poloxamer is one selected from the group consisting of: Poloxamer P367; Poloxamer P188 (a is about 80; b is about 27; average molecular weight in the range of about 7680-9510 daltons); Poloxamer P247; Poloxamer P248; Poloxamer P278; Poloxamer P308; Poloxamer P305; Poloxamer P95; Poloxamer P124 (a is about 12; b is about 20; average molecular weight in the range of about 2090-2360 daltons); Poloxamer P184; Poloxamer 237 (a is about 64; b is about 37; average molecular weight in the range of about 6840-8830 daltons); Poloxamer 338 (a is about 141; b is about 44; average molecular weight in the range of about 12,700-17,400 daltons); Poloxamer P407 (a is about 101; b is about 56; average molecular weight in the range of about 9840-14,600 daltons); Pluronic® 10R5; Pluronic® 17R2; Pluronic® 17R4; Pluronic® 25R2; Pluronic® 25R4; Pluronic® 31R1; Pluronic® F 108 Cast Solid Surfacta; Pluronic® F 108 NF; Pluronic® F 108 Pastille; Pluronic® F 108NF Prill Poloxamer 338; Pluronic® F 127 NF; Pluronic® F 127 NF 500 BHT Prill; Pluronic® F 127 NF Prill Poloxamer 407; Pluronic® F 38; Pluronic® F 38 Pastille; Pluronic® F 68; Pluronic® F 68 NF; Pluronic® F 68 NF Prill Poloxamer 188; Pluronic® F 68 Pastille; Pluronic® F 77; Pluronic® F 77 Micropastille; Pluronic® F 87; Pluronic® F 87 NF; Pluronic® F 87 NF Prill Poloxamer 237; Pluronic® F 88; Pluronic® F 88 Pastille; Pluronic® F 98; Pluronic® FT L 61; Pluronic® L 10; Pluronic® L 101; Pluronic® L 121; Pluronic® L 31; Pluronic® L 35; Pluronic® L 43; Pluronic® L 61; Pluronic® L 62; Pluronic® L 62 LF; Pluronic® L 62D; Pluronic® L 64; Pluronic® L 81; Pluronic® L 92; Pluronic® L44 NF INH surfactant Poloxamer 124; Pluronic® N 3; Pluronic® P 103; Pluronic® P 104; Pluronic® P 105; Pluronic® P 123 Surfactant; Pluronic® P 65; Pluronic® P 84; Pluronic® P 85. In some embodiments, the poloxamer can be Poloxamer P407. For example, the poloxamer can be Pluronic® F127.

The ratio of materials used for the core and the outer layer comprising a polymer depends on the nature and characteristics of the core and the outer layer. The ratios can be determined by various analysis techniques upon formation of the nanoparticle, for example, in some cases $^1$H NMR can determine the molar ratio of the monomers comprising the polymer molecules in a core and an outer layer. In some embodiments, the molar ratio of the monomers comprising the polymer molecules in the core to the outer layer is in a range from about 1:1 to about 1:50. In some embodiments, the molar ratio of the monomers comprising the polymer molecules in the core to the outer layer is in a range from about 1:5 to about 1:30. In some embodiments, the molar ratio of monomers comprising the polymer molecules in the core to the outer layer is in a range from about 1:8 to about 1:20. For example, the molar ratio of the monomers comprising the polymer molecules in the core to the outer layer can be about 1:8. In some embodiments, the molar ratio of the monomers comprising the polymer molecules in the core to the outer layer can be about 1:20.

The outer layer comprising a polymer can be used to deliver a payload by subjecting the nanoparticle to a first temperature to induce conformational changes in the outer layer of the nanoparticle that allow the payload (e.g., a biomolecule) to contact or be near the core, then subjecting the nanoparticle to a second temperature to induce conformational changes in the outer layer of the nanoparticle that encapsulate the payload with a portion of the polymer. In some embodiments, the first temperature is in a range of from about 0° C. to about 10° C. For example, the first temperature can be at about 4° C. In some embodiments, the second temperature is in a range of from about 30° C. to about 40° C. For example, the second temperature can be at about 37° C. In a non-limiting example, the preparation of a PLA-Pluronic nanoparticle loaded with a therapeutic protein is shown in FIG. **6*b*** by expanding at 4° C. to allow the therapeutic protein into nanoparticle and by contracting at 37° C. to encapsulate the therapeutic protein.

In some embodiments, the core may comprise a second payload. In some embodiments, the second payload is a biomolecule. In some embodiments, the second payload is a small molecule. In a non-limiting example, the payloads in each of the core and the outer layer may be different proteins that offer complementary therapeutic effects for a disease or condition, and can be released at different times or under diverse environmental changes, e.g., differential pH or reducing conditions. For example, the core can be used to encapsulate IL-2, and the outer layer can comprise a polymer that encapsulates IL-10. For example, the second payload could be loaded into the core prior to formation of the complete nanoparticle comprising the core and outer layer.

The nanoparticle size can be in a range from about 20 nm to about 500 nm. In some embodiments, the size can be in a range from about 40 nm to about 120 nm. In some embodiments, the size can be in a range from about 50 nm to about 90 nm.

In some embodiments, the nanoparticles present within a population, e.g., in a composition, can have substantially the same shape and/or size (i.e., they are "monodisperse"). For example, the particles can have a distribution such that no more than about 5% or about 10% of the nanoparticles have a diameter greater than about 10% greater than the average diameter of the particles, and in some cases, such that no more than about 8%, about 5%, about 3%, about 1%, about 0.3%, about 0.1%, about 0.03%, or about 0.01% have a diameter greater than about 10% greater than the average diameter of the nanoparticles.

In some embodiments, the diameter of no more than 25% of the nanoparticles varies from the mean nanoparticle diameter by more than 150%, 100%, 75%, 50%, 25%, 20%, 10%, or 5% of the mean nanoparticle diameter. It is often desirable to produce a population of nanoparticles that is relatively uniform in terms of size, shape, and/or composition so that most of the nanoparticles have similar properties. For example, at least 80%, at least 90%, or at least 95% of the nanoparticles produced using the methods described herein can have a diameter or greatest dimension that falls within 5%, 10%, or 20% of the average diameter or greatest dimension. In some embodiments, a population of nanoparticles can be heterogeneous with respect to size, shape, and/or composition.

Payloads

The methods and compositions described herein are useful for delivering a payload. In some embodiments, the payload is delivered to a biological target. The payload can be used, e.g., for labeling (e.g., a detectable agent such as a fluorophore), or for therapeutic purposes (e.g., a cytotoxin or other drug molecule).

The proportion of the payload relative to the nanoparticle depends on the characteristics of the payload, the properties of the nanoparticle, and the application. In some embodiments, the payload is loaded in the range from about 0.01% by weight to about 100.0% by weight compared with the weight of the outer layer comprising a polymer. The payload can be in the range from about 1% by weight to about 80% by weight, from about 1% by weight to about 75% by weight, from about 1% by weight to about 70% by weight, from about 1% by weight to about 65% by weight, from about 1% by weight to about 60% by weight, from about 1% by weight to about 55% by weight, from about 1% by weight to about 50% by weight, from about 1% by weight to about 45% by weight, from about 1% by weight to about 40% by weight, from about 1% by weight to about 35% by weight, from about 1% by weight to about 30% by weight, from about 1% by weight to about 25% by weight, from about 1% by weight to about 20% by weight, from about 1% by weight to about 15% by weight, from about 1% by weight to about 10% by weight, and/or from about 1% by weight to about 5% by weight compared with the weight of the outer layer comprising a polymer.

In some embodiments, the nanoparticle can comprise two payloads: a first payload encapsulated by the outer layer comprising a polymer, and a second payload encapsulated in the core. The loading of the first payload and the second payload are independently determined. In some embodiments, the first payload is loaded in the range from about 0.01% by weight to about 100.0% by weight compared with the weight of the outer layer comprising a polymer. The first payload can be in the range from about 1% by weight to about 80% by weight, from about 1% by weight to about 75% by weight, from about 1% by weight to about 70% by weight, from about 1% by weight to about 65% by weight, from about 1% by weight to about 60% by weight, from about 1% by weight to about 55% by weight, from about 1% by weight to about 50% by weight, from about 1% by weight to about 45% by weight, from about 1% by weight to about 40% by weight, from about 1% by weight to about 35% by weight, from about 1% by weight to about 30% by weight, from about 1% by weight to about 25% by weight, from about 1% by weight to about 20% by weight, from about 1% by weight to about 15% by weight, from about 1% by weight to about 10% by weight, and/or from about 1% by weight to about 5% by weight compared with the weight of the outer layer comprising a polymer. In some embodiments, the second payload is loaded in the range from about 0.01% by weight to about 100.0% by weight compared with the weight of the core. The second payload can be in the range from about 1% by weight to about 80% by weight, from about 1% by weight to about 75% by weight, from about 1% by weight to about 70% by weight, from about 1% by weight to about 65% by weight, from about 1% by weight to about 60% by weight, from about 1% by weight to about 55% by weight, from about 1% by weight to about 50% by weight, from about 1% by weight to about 45% by weight, from about 1% by weight to about 40% by weight, from about 1% by weight to about 35% by weight, from about 1% by weight to about 30% by weight, from about 1% by weight to about 25% by weight, from about 1% by weight to about 20% by weight, from about 1% by weight to about 15% by weight, from about 1% by weight to about 10% by weight, and/or from about 1% by weight to about 5% by weight compared with the weight of the core.

Drug Molecules

Drug molecules include small molecules and biomolecules. Small molecules are low molecular weight organic compounds (typically about 2000 daltons or less). In some embodiments, the molecular weight of the drug molecule is in the range from about 200 to about 2000, from about 200 to about 1800, from about 200 to about 1600, from about 200 to about 1400, from about 200 to about 1200, from about 200 to about 1000, from about 200 to about 800, from about 200 to about 600 daltons, from about 300 to about 2000, from about 300 to about 1800, from about 300 to about 1600, from about 300 to about 1400, from about 300 to about 1200, from about 300 to about 1000, from about 300 to about 800, and/or from about 300 to about 600 daltons. Examples include cytochalasin B, gramicidin D, ethidium bromide, emetine, mitomycin, etoposide, tenoposide, colchicin, daunorubicin, dihydroxy anthracin dione, mithramycin, actinomycin D, 1-dehydrotestosterone, glucocorticoids, procaine, tetracaine, lidocaine, amphotericin B, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof.

Other drug molecules include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), antifungal agents (e.g., butenafine, terbinafine, and naftifine), immunomodulating drugs (e.g., glatiramer acetate, fingolimod, teriflunomide, and dimethyl fumarate), and anti-mitotic agents (e.g., vincristine, vinblastine, paclitaxel, and maytansinoids).

Examples of suitable chemotherapeutic agents include any of: abarelix, aldesleukin, alitretinoin, allopurinol, altretamine, anastrozole, arsenic trioxide, asparaginase, azacitidine, bexarotene, bleomycin, bortezomib, busulfan, calusterone, capecitabine, carboplatin, carmustine, chlorambucil, cisplatin, cladribine, clofarabine, cyclophosphamide, cytarabine, dacarbazine, dactinomycin, dalteparin, dasatinib, daunorubicin, decitabine, denileukin, dexrazoxane, docetaxel, doxorubicin, dromostanolone, epirubicin, erlotinib, estramustine, etoposide, exemestane, filgrastim, floxuridine, fludarabine, fluorouracil, fulvestrant, gefitinib, gemcitabine, goserelin acetate, histrelin acetate, idarubicin, ifosfamide, imatinib, irinotecan, lapatinib ditosylate, lenalidomide, letrozole, leucovorin, leuprolide, levamisole, lomustine, meclorethamine, megestrol, melphalan, mercaptopurine, methotrexate, methoxsalen, mitomycin C, mitotane, mitoxantrone, nandrolone, nelarabine, nofetumomab, oxaliplatin, paclitaxel, pamidronate, pegaspargase, pegfilgrastim, pemetrexed, pentostatin, pipobroman, plicamycin, procarbazine, quinacrine, rasburicase, ruxolitinib, sorafenib, streptozocin, sunitinib, tamoxifen, temozolomide, teniposide, testolactone, thalidomide, thioguanine, thiotepa, topotecan, toremifene, tretinoin, uracil mustard, valrubicin, vinblastine, vincristine, vinorelbine, vorinostat, and zoledronate, or a pharmaceutically acceptable salt thereof.

Small molecules useful in the compositions and methods described herein bind with high affinity to a biopolymer, such as protein, nucleic acid, or polysaccharide, or other biological target. Other examples include small molecules that bind specifically to receptors for hormones, such as steroid hormones (e.g., dihydrotestosterone and estradiol), melatonin, dopamine, or other signaling molecules, that may be delivered as described herein.

Biomolecules

Biomolecules are organic molecules having a molecular weight of 200 daltons or more produced by living organisms or cells, including large polymeric molecules such as polypeptides, proteins, polysaccharides, polynucleotides and nucleic acids, or analogs or derivatives of such molecules. In some embodiments, the biomolecule is a therapeutic protein, such as an antibody, a transmembrane protein, a growth factor, an enzyme, or a structural protein. Examples that can be used in any embodiment of the disclosed compositions include cytokines, such as transforming growth factor-beta (TGF-beta), interferons (e.g., interferon-alpha, interferon-beta, interferon-gamma), colony stimulating factors (e.g., granulocyte colony stimulating factor (GM-CSF)), thymic stromal lymphopoietin (TSLP), and the interleukins, e.g., interleukin-1, interleukin-2, interleukin-3, interleukin-4, interleukin-5, interleukin-6, interleukin-7, interleukin-8, interleukin-10, interleukin-12, interleukin-13, interleukin-15, interleukin-17, interleukin-18, interleukin-22, interleukin-23, and interleukin-35; polypeptide hormones, such as amylin, anti-Müllerian hormone, calcitonin, cholecystokinin, corticotropin, endothelin, enkephalin, erythropoietin (EPO), follicle-stimulating hormone, gallanin, gastrin, ghrelin, glucagon, gonadotropin-releasing hormone, growth hormone-releasing hormone, hepcidin, human chorionic gonadotropin, human growth hormone (hGH), inhibin, insulin, insulin-like growth factor, leptin, luteinizing hormone, luteinizing hormone releasing hormone, melanocyte stimulating hormone, motilin, orexin, oxytocin, pancreatic polypeptide, parathyroid hormone, prolactin, secretin, somatostatin, thrombopoietin, thyroid-stimulating hormone, vasoactive intestinal peptide, and vasopressin; antibody-drug conjugates (e.g., trastuzumab emtansine, brentuximab vedotin, T-DM1); antibody fragment-drug conjugates; protein-drug conjugates; peptide-drug conjugates (e.g., paclitaxel-Angiopep 2, BMTP-11 (Arrowhead Research), zoptarelin doxorubicin, and NGR-hTNF); fusion proteins (i.e., a chimeric protein formed by the expression of two or more genes that encode for different proteins), e.g., Fc fusion proteins, which contain an antibody Fc unit that can offer stability or selective targeting of a cell or tissue type, including therapeutic proteins, such as atacicept, abatacept, aflibercept, alefacept, belatacept, etanercept, sotatercept, romiplostim, and rilonacept, bispecific fusion proteins (i.e., bispecific antibodies), which comprise two arms from different antibodies, and are thereby able to target two different types of antigens, such as Ec-LDP-Hr-AE, MM-111 (Merrimack Pharmaceuticals), and IMCgp100 (Immunocore Ltd.), and multimeric fusion proteins, which are fusion proteins created by engineered multimerization (e.g., with streptavidin or using leucine zippers), such as polyvalent IgG2a Fc (M045); enzymes, e.g., agalsidase beta, imiglucerase, velaglucerase alfa, taliglucerase, alglucosidase alfa, laronidase, idursulfase, and galsulfase; multimeric fusion proteins; and antibodies (e.g., monoclonal antibodies, e.g., bispecific monoclonal antibodies), including therapeutic antibodies, e.g., anticancer antibodies (e.g., abagovomab, adecatumumab, afutuzumab, alacizumab pegol, altumomab pentetate, amatuximab, anatumomab mafenatox, apolizumab, arcitumomab, bavituximab, bectumomab, belimumab, bevacizumab, bivatuzumab mertansine, blinatumomab, brentuximab vedotin, cantuzumab mertansine, cantuzumab ravtansine, capromab pendetide, cetuximab, citatuzumab bogatox, cixutumumab, clivatuzumab tetraxetan, dacetuzumab, demcizumab, detumomab, drozitumab, ecromeximab, eculizumab, elotuzumab, ensituximab, epratuzumab, etaracizumab, farletuzumab, figitumumab, flanvotumab, galiximab, gemtuzumab ozogamicin, girentuximab, ibritumomab tiuxetan, imgatuzumab, ipilimumab, labetuzumab, lexatumumab, lorvotuzumab mertansine, nimotuzumab, ofatumumab, oregovomab, panitumumab, pemtumomab, pertuzumab, tacatuzumab tetraxetan, tositumomab, trastuzumab, totumumab, zalutumumab), and anti-inflammatory antibodies (e.g., adalimumab, alemtuzumab, atlizumab, canakinumab, certolizumab, certolizumab pegol, daclizumab, efalizumab, fontolizumab, golimumab, infliximab, mepolizumab, natalizumab, omalizumab, ruplizumab, ustekinumab, visilizumab, zanolimumab, vedolizumab, belimumab, otelixizumab, teplizumab, rituximab, ofatumumab, ocrelizumab, epratuzumab, eculizumab, and briakinumab). Further examples of useful therapeutic proteins can be found in U.S. Pat. Nos. 8,349,910; and 8,043,833; US patent applications 2013/0195888; and 2007/0092486; and PCT WO 2014/130064, each of which is hereby incorporated by reference in its entirety. In some embodiments, biomolecules can be sensitive to physiological environments, e.g., to physiologic enzymes or local pH, before delivery to the target tissue or target cell.

Compositions

Provided herein is a composition comprising: a nanoparticle comprising a core and an outer layer comprising a polymer surrounding the core; and a biomolecule selectively encapsulated in the outer layer of the nanoparticle; wherein the polymer exhibits temperature-dependent conformational changes that change the size of the nanoparticle by an amount in the range from about 5% to about 500% in an aqueous medium substantially free of organic solvent.

Also provided herein is a composition comprising: a nanoparticle comprising a core and an outer layer comprising a polymer surrounding the core; and a biomolecule selectively encapsulated in the outer layer of the nanoparticle, wherein the polymer exhibits temperature-dependent conformational changes that change the size of the nanoparticle by an amount sufficient to provide for encapsulation of the biomolecule from an aqueous medium substantially free of organic solvent.

As used herein, “selectively encapsulated” refers to a payload that has a greater concentration in the outer layer than in the core. In some embodiments, a payload selectively encapsulated in the outer layer has a concentration in the range from about 60% to about 90%, from about 70% to about 90%, or from about 80% to about 90% in the outer layer compared with in the core. In some embodiments, a payload selectively encapsulated in the outer layer has a concentration that is greater than about 60%, about 70%, about 80%, about 90%, about 95%, about 98%, or about 99% in the outer layer compared with in the core.

The disclosure also provides a composition comprising a nanoparticle comprising a core, an outer layer comprising a polymer surrounding the core and a biomolecule encapsulated in the outer layer, wherein the composition is prepared by a process comprising: (a) preparing a composition comprising a nanoparticle comprising a core and an outer layer comprising a polymer surrounding the core; an aqueous medium substantially free of organic solvent; and a biomolecule dissolved or suspended in the aqueous medium; (b) subjecting the composition to a first temperature at which the polymer expands to allow entry of the biomolecule into the outer layer; and (c) subjecting the composition to a second temperature at which the polymer contracts to encapsulate the biomolecule in the outer layer.

The compositions of the disclosure offer the ability to deliver biomolecules, for example, therapeutically useful proteins, that may be sensitive to organic solvents without exposure to the solvents which are needed in other preparations. Such compositions retain a high bioactivity of the biomolecule compared with the native form but with an enhanced stability. In some embodiments, the bioactivity of the biomolecule in the composition is in a range from about 70% to about 100%, from about 80% to about 100%, or from about 90% to about 100% of the bioactivity of a native biomolecule. In some embodiments, the bioactivity of the biomolecule in the composition is about 90%, about 95%, about 97%, or greater than 99% of the bioactivity of a native biomolecule. Thus, in some aspects there are provided compositions as described herein comprising a nanoparticle comprising a core and an outer layer comprising a polymer surrounding the core; and a biomolecule selectively encapsulated in the outer layer of the nanoparticle, wherein the bioactivity of the biomolecule in the composition is in a range from about 70% to about 100%, from about 80% to about 100%, or from about 90% to about 100% of the bioactivity of a native biomolecule, or wherein the bioactivity of the biomolecule in the composition is about 90%, about 95%, about 97%, or greater than 99% of the bioactivity of a native biomolecule.

The compositions of the disclosure can provide for controlled release or sustained release of a biomolecule in a biological system, e.g., when a biomolecule is delivered to a subject in need of therapy. Controlled release refers to delivery of an agent at a controlled rate for an extended time or in response to a stimulus (e.g., upon a change in pH or temperature, or in the presence of an enzyme). Controlled release of a biomolecule can provides a well-characterized and reproducible dosage form. Sustained release refers to the release of an agent over an extended period of time. In sustained release, the rate and duration of biomolecule release can be controlled to achieve a particular profile. A sustained release profile can include zero-order release, exponential decay, step-function release, or other release profiles that carry over a period of time, e.g., one to several hours (e.g., about 8 hours or 24 hours), one to several days (e.g., about 2, 3, 4, 5, 6, 7, 10, or 14 days), one to several weeks (e.g, about 2, 3, or 4 weeks) or one to several months (e.g., about 2, 3, 4, 5, or 6 months). The terms "zero-order release", "exponential decay" and "step-function release" as well as other sustained release profiles are well known in the art.

The controlled release profiles can afford enhanced pharmacokinetic profiles of a biomolecule within a subject, compared with a biomolecule in a subject that has not been loaded into a TNP. An enhanced pharmacokinetic profile can exhibit an improved property of one or more selected from AUC, half-life, clearance, mean residence time, and volume of distribution (Vss). In some embodiments, the AUC of a biomolecule in a composition of the disclosure is in a range from about 100% to about 1000%, from about 150% to about 700%, or from about 200% to about 500% of the AUC of a native biomolecule, or wherein the AUC of the biomolecule in the composition is about 150%, about 200%, about 250%, about 300%, about 350%, about 400%, about 450%, about 500%, or greater than 500% of the AUC of a native biomolecule. In some embodiments, the half-life of a biomolecule in a composition of the disclosure is in a range of from about 100% to about 100,000%, from about 100% to about 1000%, from about 100% to about 500%, from about 150% to about 400%, or from about 200% to about 300% of the half-life of a native biomolecule, or wherein the half-life of the biomolecule in the composition is about 150%, about 200%, about 250%, about 300%, or greater than 400% of the half-life of a native biomolecule. In some embodiments, the clearance of a biomolecule in a composition of the disclosure is in a range from about 1% to about 100%, from about 10% to about 90%, from about 20% to about 80%, from about 30% to about 70%, or from about 40% to about 80% of the clearance of a native biomolecule, or wherein the clearance of the biomolecule in the composition is about 3%, about 5%, about 10%, about 15%, about 20%, about 25%, about 30%, about 40%, about 50%, about 60%, about 70%, or about 80% of the clearance of a native biomolecule. In some embodiments, the mean residence time of a biomolecule in a composition of the disclosure is in a range from about 100% to about 1000%, from about 150% to about 700%, or from about 200% to about 500% of the mean residence time of a native biomolecule, or wherein the mean residence time of the biomolecule in the composition is about 150%, about 200%, about 250%, about 300%, about 350%, about 400%, about 450%, about 500%, or greater than 500% of the mean residence time of a native biomolecule.

Methods of Making

This disclosure provides a method comprising: (a) preparing a composition comprising a nanoparticle comprising a core and an outer layer comprising a polymer surrounding the core; an aqueous medium substantially free of organic solvent; and a biomolecule dissolved or suspended in the aqueous medium; (b) subjecting the composition to a first temperature at which the polymer expands to allow entry of the biomolecule into the outer layer; and (c) subjecting the composition to a second temperature at which the polymer contracts to encapsulate the biomolecule in the outer layer.

The nanoparticles of the disclosure can be made by self-assembly under one-step nanoprecipitation methods described herein. The process can avoid use of detergents, sonication, or other harsh formulation techniques, and thus offers a simple and convenient synthetic approach which may be amenable to clinical use.

A nanoparticle can be prepared without the desired payload (e.g., the biomolecule) first, by dissolving or suspending the nanoparticle in an organic solvent mixture, e.g., a solution of Plutonic F127 and PLA in acetone, then adding the mixture to an excess of water, thus nanoprecipitating the platform nanoparticles comprising a core and an outer layer comprising a polymer surrounding the core. The nanoparticles self-assemble upon exposure to the aqueous environment. Once formed, the nanoparticles can be purified and made substantially free of organic solvent by methods known in the art, e.g., centrifugation and filtration.

The nanoparticle can then be placed into an aqueous medium containing a payload, for example, a biomolecule which has been dissolved or suspended in the aqueous medium, and subjected to a first temperature, which allows the polymer in the outer layer to expand. The biomolecule would thus be allowed at the conditions of the first temperature to enter the outer layer. The aqueous medium containing the nanoparticle and the biomolecule can then be subjected to a second temperature to contract the outer layer polymer, thus encapsulating the biomolecule in the outer layer. The first temperature and the second temperature are each in a range of from about 0° C. to about 100° C. In some embodiments, the first temperature and the second temperature are each in a range of from about 0° C. to about 50° C. The expansion of the outer layer of the nanoparticle to allow entry of the biomolecule can occur, e.g., at a temperature in the range from about 0° C. to about 20° C., from about 0° C. to about 15° C., from about 0° C. to about 10° C., from about 0° C. to about 5° C., e.g., at about 0° C., 1° C., 2° C., 3° C., 4° C. or 5° C. The contraction of the outer layer of the nanoparticle to encapsulate the biomolecule can occur, e.g., at a temperature in the range from about 10° C. to about 50° C., from about 20° C. to about 50° C., from about 30° C. to about 50° C., from about 15° C. to about 45° C., from about 25° C. to about 45° C., from about 35° C. to about 45° C., from about 30° C. to about 40° C., or from about 35° C. to about 40° C., e.g., at about 35° C., 36° C., 37° C., 38° C., 39° C. or 40° C. For example, the first temperature can be at about 4° C., and the second temperature can be at about 37° C.

This method offers an advantage in that the introduction of the payload, e.g., a biomolecule, can be performed after formation and purification of the nanoparticle. Further, the introduction of the payload can be performed under mild temperature changes, and the need for additional steps such as sonication can be avoided. In such a manner, the payload can be encapsulated into a nanoparticle under conditions wherein it does not encounter organic solvents or harsh conditions such as sonication, each of which may degrade or deactivate a sensitive payload, such as a therapeutic protein, which may undergo chemical or conformational changes that lower the biological activity of the payload when exposed to organic solvents or detergents or conditions such as high temperature or sonication.

In some embodiments, the polymer can be a poloxamer, such as Poloxamer P407, Poloxamer P367, Poloxamer P188, Poloxamer P247, Poloxamer P248, Poloxamer P278, Poloxamer P308, Poloxamer P305, Poloxamer P95, Poloxamer P124, Poloxamer P184, or a Pluronic® polymer (e.g., Pluronic® F127, F68, F87, F88, F98, F108, P105, L35, L44, and L64), that can expand at a first temperature for preparation, and contract at a second temperature to encapsulate and protect a biomolecule for delivery. The first temperature and the second temperature are each in a range of from about 0° C. to about 100° C. In some embodiments, the first temperature and the second temperature are each in a range of from about 0° C. to about 50° C. The expansion of the outer layer of the nanoparticle to allow entry of the biomolecule can occur, e.g., at a temperature in the range from about 0° C. to about 20° C., from about 0° C. to about 15° C., from about 0° C. to about 10° C., from about 0° C. to about 5° C., e.g., at about 0° C., 1° C., 2° C., 3° C., 4° C. or 5° C. The contraction of the outer layer of the nanoparticle to encapsulate the biomolecule can occur, e.g., at a temperature in the range from about 10° C. to about 50° C., from about 20° C. to about 50° C., from about 30° C. to about 50° C., from about 15° C. to about 45° C., from about 25° C. to about 45° C., from about 35° C. to about 45° C., from about 30° C. to about 40° C., or from about 35° C. to about 40° C., e.g., at about 35° C., 36° C., 37° C., 38° C., 39° C. or 40° C. In a non-limiting example, as shown in FIG. 6*b*, Pluronic® F127 may expand at a first temperature of about 4° C. to allow for a biomolecule, such as interleukin-2, to approach the core. The composition may then be subjected to a second temperature at about 37° C. to contract the polymer, thus selectively encapsulating the biomolecule in the outer layer of the nanoparticle.

Methods of Use

The methods of the disclosure offer the ability to deliver a payload, e.g., a biomolecule, to the desired biological target without exposing the payload to non-aqueous solvents.

This disclosure provides for a method of delivering a payload to a cell, comprising contacting the cell with an effective amount of a composition as described herein. In some embodiments, the contacting is in vitro. In some embodiments, the contacting is in vivo. In some embodiments, the cell is a blood cell, a cancer cell, and immune cell (e.g., a macrophage cell), an epithelial cell (e.g., a skin cell), a bacterial cell, or a virus-infected cell.

In some embodiments, the cell is a macrophage cell. For example, the macrophage cell can be a RAW 264.7 cell. The macrophage cell can be unstimulated or stimulated by, for example, lipopolysaccharide (LPS).

In some embodiments, the cell is a cancer cell. In some embodiments, the cancer cell is selected from a breast cancer cell, a colon cancer cell, a leukemia cell, a bone cancer cell, a lung cancer cell, a bladder cancer cell, a brain cancer cell, a bronchial cancer cell, a cervical cancer cell, a colorectal cancer cell, an endometrial cancer cell, an ependymoma cancer cell, a retinoblastoma cancer cell, a gallbladder cancer cell, a gastric cancer cell, a gastrointestinal cancer cell, a glioma cancer cell, a head and neck cancer cell, a heart cancer cell, a liver cancer cell, a pancreatic cancer cell, a melanoma cancer cell, a kidney cancer cell, a laryngeal cancer cell, a lip or oral cancer cell, a lymphoma cancer cell, a mesothioma cancer cell, a mouth cancer cell, a myeloma cancer cell, a nasopharyngeal cancer cell, a neuroblastoma cancer cell, an oropharyngeal cancer cell, an ovarian cancer cell, a thyroid cancer cell, a penile cancer cell, a pituitary cancer cell, a prostate cancer cell, a rectal cancer cell, a renal cancer cell, a salivary gland cancer cell, a sarcoma cancer cell, a skin cancer cell, a stomach cancer cell, a testicular cancer cell, a throat cancer cell, a uterine cancer cell, a vaginal cancer cell, and a vulvar cancer cell. For example, the cancer cell can be a breast cancer cell, such as an MCF-7 cell.

The present disclosure also provides for a method of treating a disease or condition in a subject in need thereof, comprising administering to the subject a therapeutically effective amount of a composition as described herein.

As used herein, a subject is a mammal, which can include a mouse, a rat, a guinea pig, a farm animal, such as a pig, a goat, a horse, or a cow, a non-human primate, such as a cynomolgus monkey, or a human. In some embodiments, the subject is a human.

The compositions of the disclosure may be used in any method of treating a disease or condition beneficially treated by administration of a payload, e.g., a biomolecule, in a subject.

In some embodiments, a biomolecule can be a polypeptide, a protein, or a nucleic acid. In some embodiments, the biomolecule can be a cytokine, such as transforming growth factor-beta (TGF-beta), an interferon (e.g., interferon-alpha, interferon-beta, interferon-gamma), a colony stimulating factor (e.g., granulocyte colony stimulating factor (GM-CSF)), thymic stromal lymphopoietin (TSLP), and an interleukin (e.g., interleukin-1, interleukin-2, interleukin-3, interleukin-4, interleukin-5, interleukin-6, interleukin-7, interleukin-8, interleukin-10, interleukin-12, interleukin-13, interleukin-15, interleukin-17, interleukin-18, interleukin-22, interleukin-23, and interleukin-35).

The biomolecule can be useful to treat an inflammatory disease or condition. While improvements in recent years have led to advancements in the treatment of inflammatory diseases, significant challenges remain. See, for example, Tabas, I; Glass, C. K. Anti-Inflammatory Therapy in Chronic Disease: Challenges and Opportunities. *Science* 339 (6116): 166-172 (2013), which is herein incorporated by reference in its entirety. In some embodiments, the biomolecule is a cytokine useful to treat an inflammatory disease, e.g., an interleukin selected from the group consisting of: interleukin-2, interleukin-10, and interleukin-12. In some embodiments, the biomolecule is a therapeutic antibody or an Fc fusion protein useful in the treatment of an inflammatory disease. Anti-inflammatory antibodies include adalimumab, alemtuzumab, atlizumab, canakinumab, certolizumab, certolizumab pegol, daclizumab, efalizumab, fontolizumab, golimumab, infliximab, mepolizumab, natalizumab, omalizumab, ruplizumab, ustekinumab, visilizumab, zanolimumab, vedolizumab, belimumab, otelixizumab, teplizumab, rituximab, ofatumumab, ocrelizumab, epratuzumab, eculizumab, and briakinumab. Exemplary useful Fc fusion proteins to treat inflammatory diseases include atacicept, abatacept, alefacept, etanercept, and rilonacept.

The methods of the present disclosure can be used to treat an inflammatory disease, which includes arthritis, multiple sclerosis, rheumatoid arthritis, psoriasis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis, Paget's disease of bone, palindromic rheumatism, patellofemoral pain syndrome, Pellegrini-Stieda syndrome, pigmented villonodular synovitis, *piriformis* syndrome, plantar fasciitis, polyarteritis nodos, polymyalgia rheumatica, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, reperfusion injury, retrocalcaneal bursitis, rheumatic fever, rheumatoid vasculitis, rotator cuff tendinitis, sacroiliitis, *salmonella* osteomyelitis, sarcoidosis, saturnine gout, Scheuermann's osteochondritis, scleroderma, septic arthritis, seronegative arthritis, *shigella* arthritis, shoulder-hand syndrome, sickle cell arthropathy, Sjogren's syndrome, slipped capital femoral epiphysis, spinal stenosis, spondylolysis, *staphylococcus* arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis. Inflammatory diseases or conditions with an inflammatory component not triggered by autoimmunity are also included. See, for example, Tabas, I; Glass, C. K. *Science* 339 (6116): page 169 (2013):

Chronic diseases associated with an inflammatory component not directly induced by an auto-immune process are the most common diseases of aging and represent our greatest health threats. These include most forms of cardiovascular disease, type 2 diabetes, and virtually all neurodegenerative diseases. In each case, a nonautoimmune primary pathological process—for example, excess subendothelial apolipoprotein B—containing lipoproteins, saturated fatty acids, or formation of protein aggregates, respectively—results in the generation of DAMPs [damage-associated molecular patterns] that are detected by PRRs [pattern recognition receptors]. Moreover, the inflammatory response itself may amplify the production of disease-specific DAMPs, resulting in positive-feedback loops that accelerate the underlying disease process. For example, inflammation promotes formation of oxidized phospholipids that may serve asimportant DAMPs in atherosclerosis and may enhance the formation of β-amyloid and tau aggregates in Alzheimer's disease.

The biomolecule can be useful to treat a cancer. In some embodiments, the biomolecule is a therapeutic monoclonal antibody, including, but not limited to, abagovomab, adecatumumab, afutuzumab, alacizumab pegol, altumomab pentetate, amatuximab, anatumomab mafenatox, apolizumab, arcitumomab, bavituximab, bectumomab, belimumab, bevacizumab, bivatuzumab mertansine, blinatumomab, brentuximab vedotin, cantuzumab mertansine, cantuzumab ravtansine, capromab pendetide, cetuximab, citatuzumab bogatox, cixutumumab, clivatuzumab tetraxetan, dacetuzumab, demcizumab, detumomab, drozitumab, ecromeximab, eculizumab, elotuzumab, ensituximab, epratuzumab, etaracizumab, farletuzumab, figitumumab, flanvotumab, galiximab, gemtuzumab ozogamicin, girentuximab, ibritumomab tiuxetan, imgatuzumab, ipilimumab, labetuzumab, lexatumumab, lorvotuzumab mertansine, nimotuzumab, ofatumumab, oregovomab, panitumumab, pemtumomab, pertuzumab, tacatuzumab tetraxetan, tositumomab, trastuzumab, totumumab, zalutumumab.

The methods of the disclosure can be used to treat a cancer in a subject. Cancers include, but are not limited to, a breast cancer, a colon cancer, a leukemia, a bone cancer, a lung cancer, a bladder cancer, a brain cancer, a bronchial cancer, a cervical cancer, a colorectal cancer, an endometrial cancer, an ependymoma, a retinoblastoma, a gallbladder cancer, a gastric cancer, a gastrointestinal cancer, a glioma, a head and neck cancer, a heart cancer, a liver cancer, a pancreatic cancer, a melanoma, a kidney cancer, a laryngeal cancer, a lip or oral cancer, a lymphoma, a mesothioma, a mouth cancer, a myeloma, a nasopharyngeal cancer, a neuroblastoma, an oropharyngeal cancer, an ovarian cancer, a thyroid cancer, a penile cancer, a pituitary cancer, a prostate cancer, a rectal cancer, a renal cancer, a salivary gland cancer, a sarcoma, a skin cancer, a stomach cancer, a testicular cancer, a throat cancer, a uterine cancer, a vaginal cancer, and a vulvar cancer.

The delivery of a biomolecule in a subject can also be used in the treatment of a disease or condition that can be beneficially treated by administration of a growth hormone. The disease or condition can be characterized by an insufficient amount of growth hormone, e g., human growth hormone (hGH). For example, hGH can be used as a replacement therapy in children or adults with an hGH deficiency. The methods of the disclosure can also be used to deliver, e.g., human growth hormone to treat conditions which produce short stature but is not related to deficiencies in hGH, or in maintaining muscle mass to ameliorate muscle wasting as a result of diseases such as AIDS.

The methods of the disclosure are useful to deliver insulin in the treatment of diabetes, which includes type 1, type 2, gestational, surgically induced, and chemically induced diabetes, and latent autoimmune diabetes in adults (LADA or type 1.5 diabetes).

EXAMPLES

Materials and General Methods

Poly(D,L-lactide-co-glycolide) (50:50) with terminal carboxylate groups (PLGA-COOH, inherent viscosity 0.18 dL/g in hexafluoroisopropanol, Mw ~6.7 kDa) and poly(D, L-lactide) with terminal carboxylate groups (PLA-COOH, inherent viscosity 0.21 dL/g in chloroform, Mw ~18 kDa) were purchased from Durect Lactel® Absorbable Polymers (Pelham, Ala., USA). Poly(D,L-lactide) with terminal amine groups (PLA-$NH_2$, Mw ~19 kDa) was obtained from Akina, Inc. (West Lafayette, Ind., USA). Pluronic® F 127 (PF 127), lysozyme from chicken egg whites, and lipopolysaccharides (LPS) from *Escherichia coli* 0111:B4 were purchased from Sigma-Aldrich (St. Louis, Mo., USA). As model therapeutic proteins, recombinant mouse interleukin 10 [IL-10, Mw ~36 kDa, isoelectric point (pI) 7.9] from R&D Systems, Inc. (Minneapolis, Minn., USA) and recombinant human erythropoietin (EPO, Mw ~35 kDa, pI 8.3), human insulin (Mw ~6 kDa, pI 5.3), and human growth hormone (hGH, Mw ~22 kDa, pI 5.2) from Sigma-Aldrich were used. Enzyme-linked immunosorbent assay (ELISA) kits for IL-10, EPO, and hGH were obtained from R&D Systems, Inc. (Minneapolis, Minn., USA), and an Insulin ELISA kit was purchased from EMD Millipore (Billerica, Mass., USA). Reactive oxygen species (ROS) detection reagent [2',7'-Dichlorodihydrofluorescein diacetate (DCF$H_2$-DA)] was obtained from Invitrogen (Carlsbad, Calif., USA). For qPCR analysis, all primers were purchased from Integrated DNA Technologies, Inc. (IDT®, Coralville, Iowa, USA). All chemicals were of analytical grade and were used without further purification.

The macrophage cell line RAW 264.7 and human breast cancer cell line MCF-7 were obtained from American Type Culture Collection (ATCC, Manassas, Va., USA) and then cultured in Dulbecco's modified Eagle's medium (DMEM, ATCC) including 10% heat-inactivated fetal bovine serum (FBS, Gibco, Grand Island, N.Y., USA) in a cell culture incubator (37° C. and 5% $CO_2$).

Charge Potential Determinations

The hydrodynamic diameters and surface charges (ζ-potentials) of TNPs and protein-loaded TNPs (2 mg/mL) in de-ionized water were analyzed at 25° C. by quasi-electric laser light scattering using a ZetaPALS dynamic light-scattering detector (15 mW laser, incident beam of 676 nm; Brookhaven Instruments Corporation, Holtsville, N.Y., USA). In addition, the thermosensitive swelling/deswelling behavior of TNPs was analyzed from 4° C. to 37° C. All measurements were carried out in triplicate.

Transmission Electron Microscopy

The size and morphology of TNPs were also assessed by transmission electron microscopy (TEM, Tecnai™ G2 Spirit BioTWIN, FEI Company, Hillsboro, Oreg., USA) operating at 80 kV. To identify the core-sponge shell structure of the nanoparticles, the nanoparticle solution (2 mg/mL) was mixed with 2% (w/v) phosphotungstic acid solution at 1:1 volume ratio and incubated at room temperature for 10 min for negative staining. Then the TEM sample was prepared by adding 20 μL of the stained nanoparticle suspension onto a 200-mesh formvar/carbon-coated copper grid at room temperature. The excess solution was removed with filter paper and air-dried prior to detection.

Example 1

Synthesis of Thermosponge Nanoparticles

Thermosponge nanoparticles (TNPs) composed of PLA (PLA-COOH or PLA-$NH_2$) as a core and Pluronic F127 as an outer shell layer were prepared by the nanoprecipitation method. The PLA solution (10 mg/mL in acetone) was mixed with the Pluronic F127 for 4 h at room temperature. The reaction mixture was then added dropwise to 5 mL of nuclease-free water (HyClone®, de-ionized water) under gentle stirring. TNPs were stirred for 6 h and centrifuged under 2,700×g for 20 min using Amicon Ultra-15 centrifugal filters (EMD Millipore, MWCO 100 kDa) to remove the unbound Pluronic F127. The resulting TNPs were resuspended in 3 mL of nuclease-free water and filtered through sterile 0.2 μm syringe filters.

Figure 2:
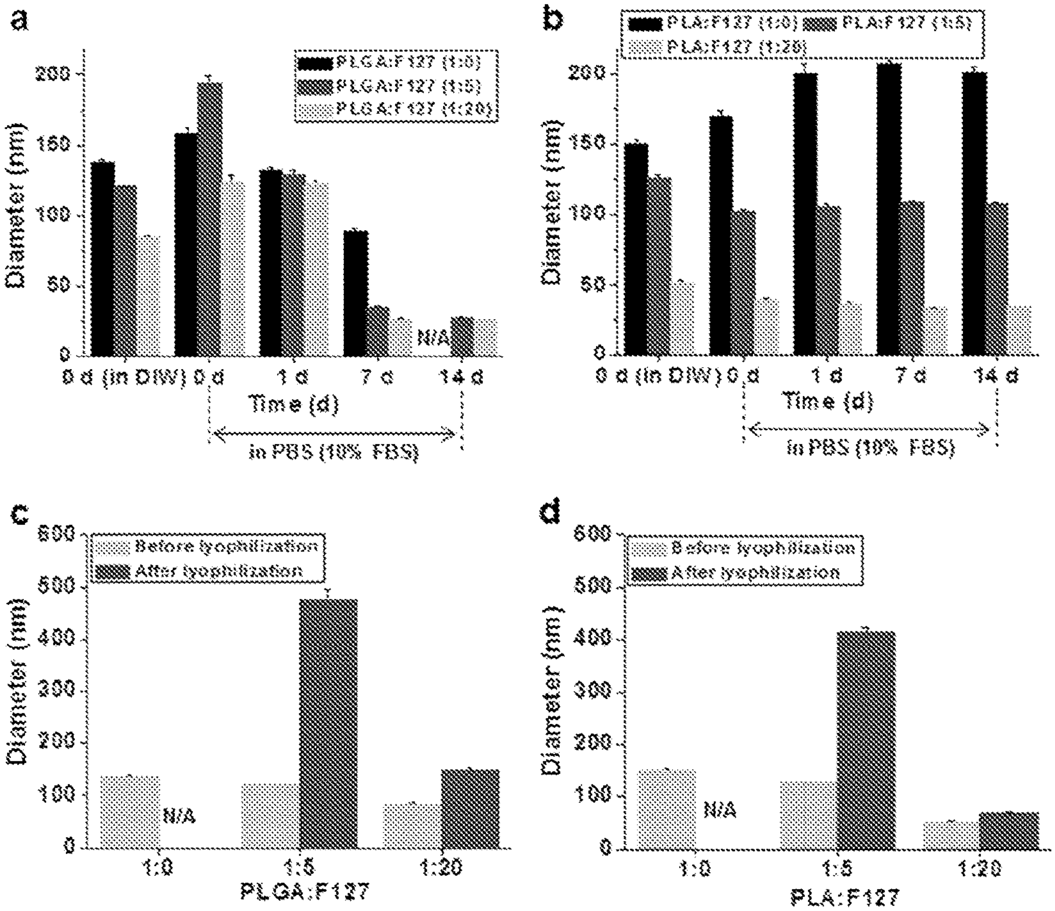
FIG. 2 shows stability analysis results for TNPs.
Figure 3:
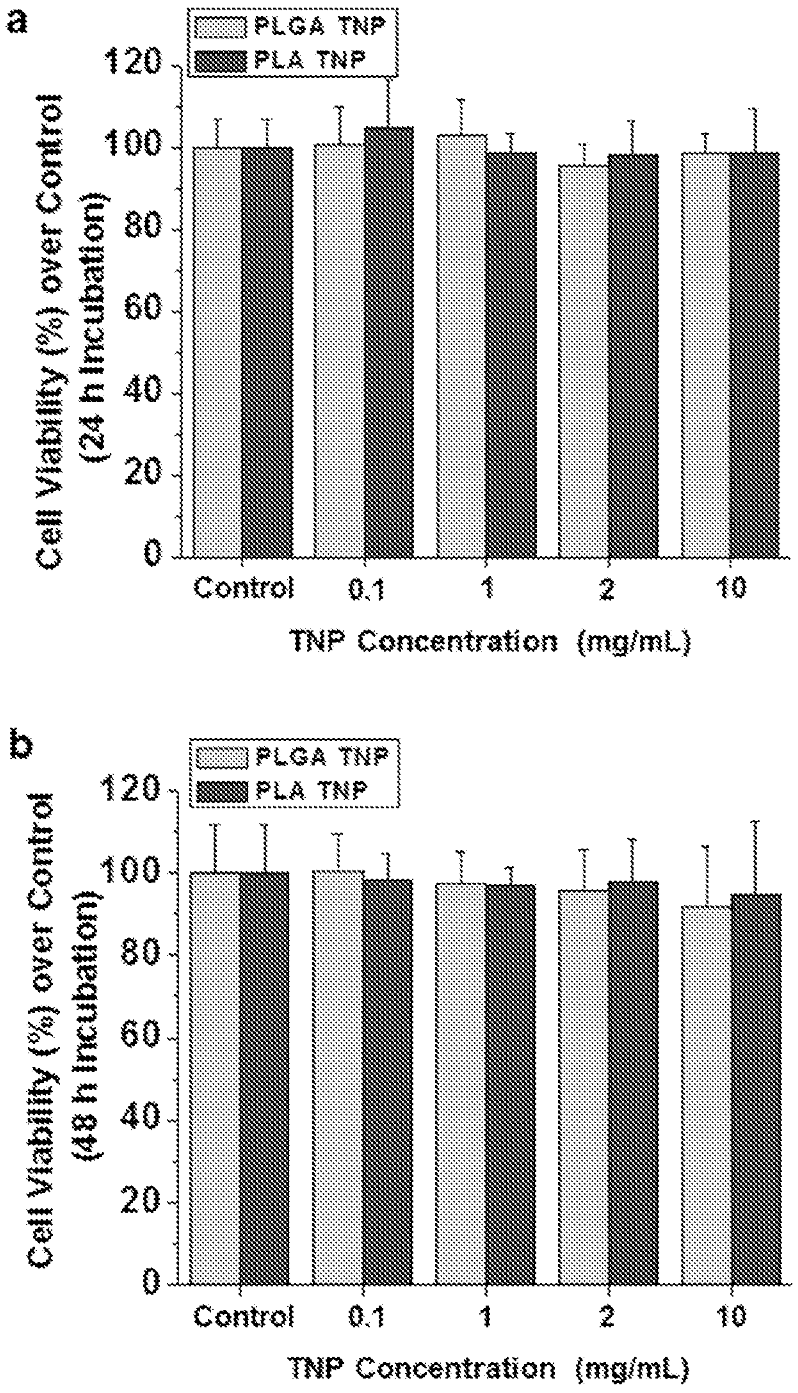
FIG. 3 shows cytotoxicity of TNPs. The cytotoxicity of PLGA-based and PLA-based thermosponge nanoparticles (TNPs, 1:20 ratio of core to outer layer) was analyzed on RAW 264.7 macrophage cells for 24 h (FIG. 3*a*) and 48 h (FIG. 3*b*) incubation (n=3).

The composition ratio of the core and shell layer was evaluated for the preparation of TNPs with stability and small size (<100 nm), using PLGA or PLA with carboxy terminals as a core component, and Pluronic F127 as a shell component. The TNPs were developed in various sizes, with core polymer:shell polymer ratios varying from 1:0 to 1:20. Size and zeta potentials ranged from 151±4 nm, −31.2±0.6 mV (in the case of PLA-based TNPs, 1:0) and 137±3 nm, −55.5±3.2 mV (in the case of PLGA-based TNPs, 1:0), to 51±3 nm, −10.3±0.9 mV (in the case of PLA-based TNPs, 1:20) and 84±1 nm, −23.5±3.2 mV (in the case of PLGA-based TNPs, 1:20) (FIG. 1). Notably, in the case of PLA-based TNPs, the nanoparticles (at both 1:5 and 1:20 core: outer shell ratios) were more stable than PLGA-based TNPs in PBS with 10% FBS, as well as in a resuspended state after lyophilization, indicating a stronger interaction between the PLA and Pluronic F127 polymers (FIG. 2). In the cytotoxicity test, nanoparticles ranging from 0.1 to 10 mg/mL did not affect the metabolic activity of RAW 264.7 macrophage cells for both 24 h and 48 h (FIG. 3).

Figure 4:
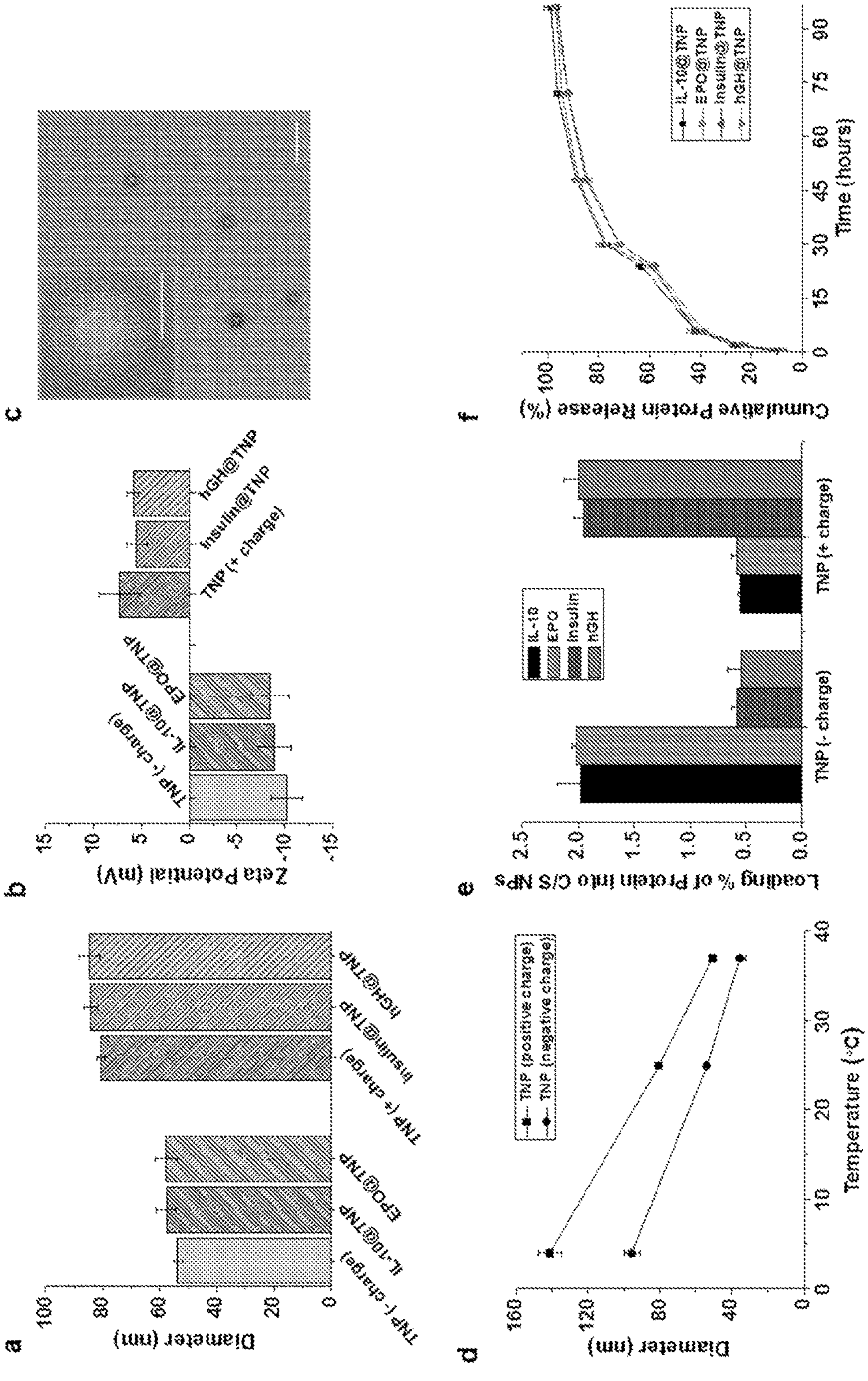
FIG. 4 shows the characterization of TNPs.
Figure 5:
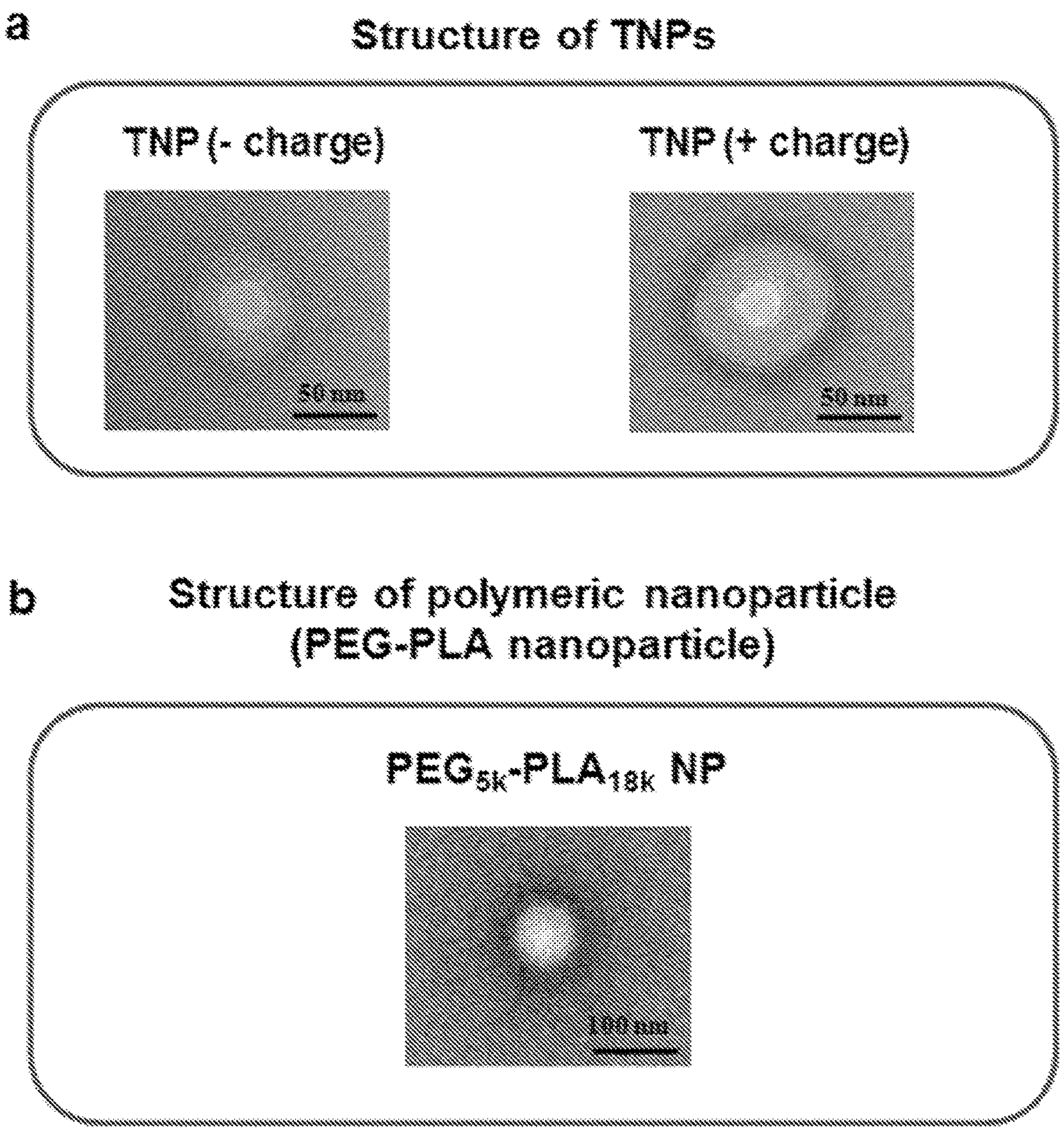
FIG. 5 shows the structure of TNPs. Comparison of TEM images (high magnification) of TNPs (FIG. 5*a*), and comparative example PEG-PLA nanoparticles (FIG. 5*b*). Nanoparticles were stained with 2% (w/v) phosphotungstic acid solution at 1:1 volume ratio and analyzed by TEM machine operating at 80 kV.

TNPs (1:20 ratio), optimized for physicochemical characteristics and stability, were prepared by the nanoprecipitation method as described above. In the case of the negatively charged TNPs (PLA-COOH as a core), the hydrodynamic size and surface charge were 54±1 nm and −10.2±1.6 mV, respectively, whereas the positively charged TNPs (PLA-$NH_2$ as a core) were 81±1 nm in size and had a surface charge of 7.3±2.1 mV (FIGS. 4*a* and 4*b*). Interestingly, both TNPs demonstrated similar temperature-responsive swelling/deswelling Pluronic shell behavior such as ~96 nm at 4° C., ~54 nm at 25° C., and ~35 nm at 37° C. (in the case of negatively charged TNPs) and ~141 nm at 4° C., ~81 nm at 25° C., and ~51 nm at 37° C. (in the case of positively charged TNPs) (FIG. 4*d*). In addition, the morphological characteristics of TNPs were assessed using transmission electron microscopy (TEM) after negative staining (FIG. 4*c*). TEM images indicated a spherical core-sponge shell structure for the negatively charged nanoparticles, and similar diameters were obtained with dynamic light scattering. The positively and negatively charged TNPs showed very similar results. The core-sponge shell structure is also clearly visible in the high-magnification image in the inset of FIG. 4*c* and easily discriminated when compared with the morphology of PEG-PLA nanoparticles (FIG. 5).

Example 2

Protein Loading of Thermosponge Nanoparticles

Figure 6:
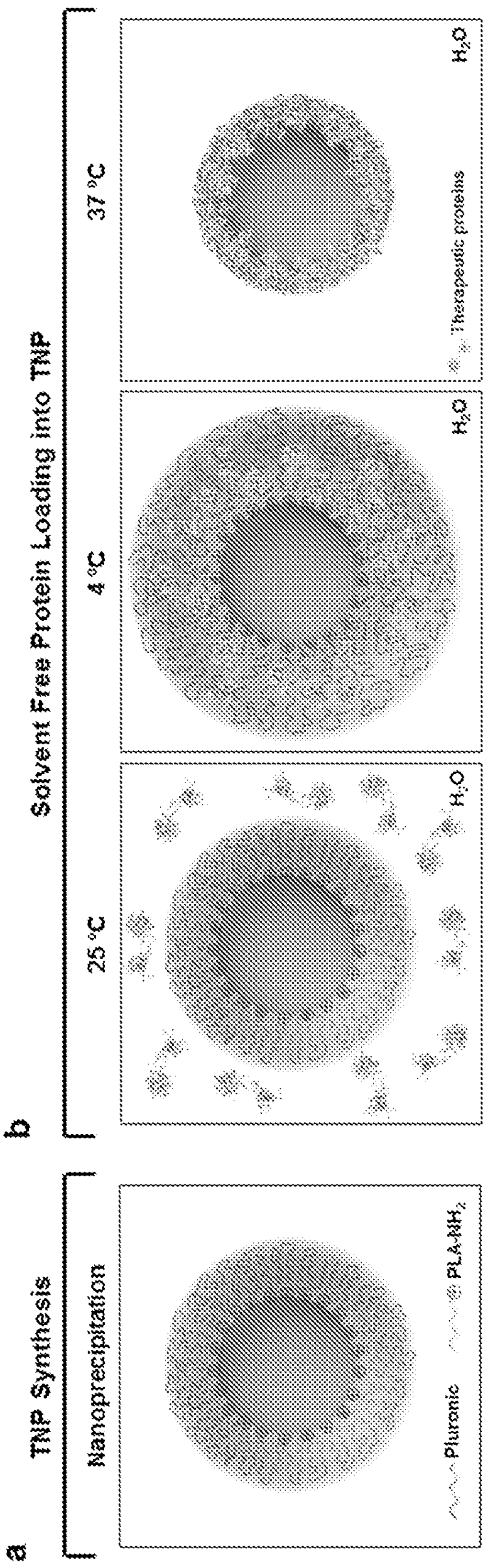
FIG. 6 shows a schematic illustration of a TNP platform.

A schematic for the approach for protein loading onto the thermosponge nanoparticle is shown in FIG. 6. For preparation of protein-loaded TNPs via a solvent-free encapsulation method, therapeutic proteins such as IL-10 and EPO were selected for negatively charged TNPs (PLA-COOH as a core), and proteins such as insulin and hGH were selected for positively charged TNPs (PLA-$NH_2$ as a core). As shown in FIG. 4, each type of TNP (500 μg/50 μL) was mixed with each protein (11 μg/55 μL) in de-ionized water and then incubated at 4° C. for 2 hours without any organic solvents. The protein encapsulation efficiency and the loading content were determined by separation of unloaded proteins from TNPs using Amicon Ultra centrifugal filters (MWCO 100 kDa). Unloaded proteins were measured using a protein ELISA kit and Synergy HT multi-mode microplate reader (BioTek Instruments Inc., Winooski, Vt., USA) at 450 rim absorbance.

Figure 7:
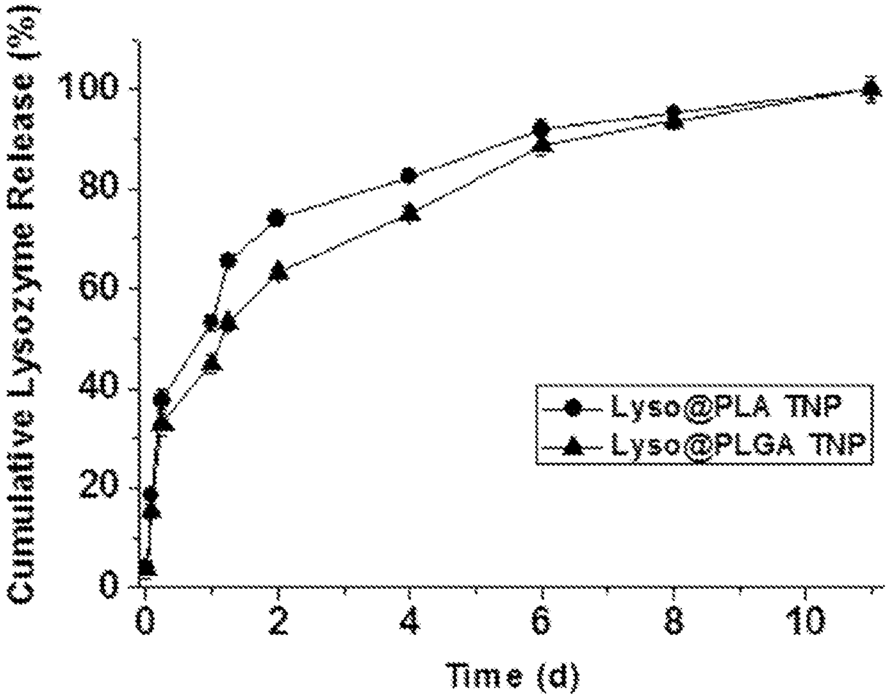
FIG. 7 shows release profiles of lysozyme as a model protein drug from the thermosponge nanoparticles (1:20 ratio of core to outer layer) in PBS buffer (pH 7.4) at 100 rpm and 37° C. (n=3). Lyso@PLA is lysozyme loaded onto a PLA nanoparticle; Lyso@PLGA is lysozyme loaded onto a PLGA nanoparticle.

Using lysozyme as a model protein, the TNPs showed high encapsulation efficiency (90%) and loading content (1.8 wt %), with positive charge and controlled-release kinetics up to a week (FIG. 7).

Therapeutic proteins (both positively charged IL-10 and EPO and negatively charged insulin and hGH) were loaded into each type of TNP without organic solvents, using two driving forces: (1) the electrostatic interaction between a negatively charged or positively charged PLA core and slightly positively charged or negatively charged proteins in de-ionized water (FIG. 4*e*) and (2) the volume expansion of the Plutonic F127 shell at low temperature (FIG. 4*d*). After loading the proteins into TNPs, the unencapsulated proteins were separated by ultra-filtration and analyzed for loading content (~2.0 wt %) (FIG. 4*e*) and encapsulation efficiency (~90%). The physicochemical parameters (size, surface charge, and morphology) of the TNPs were not substantially affected by loading the proteins into the TNPs (protein@TNP).

Example 3

Release of Proteins from Thermosponge Nanoparticles

To analyze the release profiles of the proteins loaded into TNPs, each TNP (25 μg/50 μL) was mixed with the proteins (500 ng/50 μL), including slightly positively charged proteins (IL-10 or EPO) or slightly negatively charged proteins (insulin or hGH), in de-ionized water and then incubated at 4° C. for 2 hours. The protein-loaded nanoparticles were dispersed in 1 mL of phosphate-buffered saline solution (PBS) and subsequently incubated in a shaking incubator at 100 rpm and 37° C. At each time point, the protein released from nanoparticles was isolated using Amicon Ultra-0.5 centrifugal filters (MWCO 50 kDa) at 5,000 rpm for 2 min at 20° C. Then the protein-loaded nanoparticles were resuspended in PBS and incubated in the same manner until the last defined time point. The amount of released protein at each time point was measured at 450 nm using an ELISA kit. The measurements were done in triplicate.

The release profiles of the proteins from the nanoparticles showed similar patterns of sustained release for four days without an initial burst, supporting their use in therapeutic regimens for various diseases (FIG. 4*f*). Based on these successful results, the biological integrity of IL-10 and insulin proteins was further investigated, as IL-10 has been shown to be a highly potent anti-inflammatory cytokine with potential therapeutic affects in atherosclerosis treatment[11], and successful insulin delivery is also deemed a highly important unmet medical need[5].

Example 4

Effect of IL-10 in Reactive Oxygen Species (ROS) Assay

Figure 8:
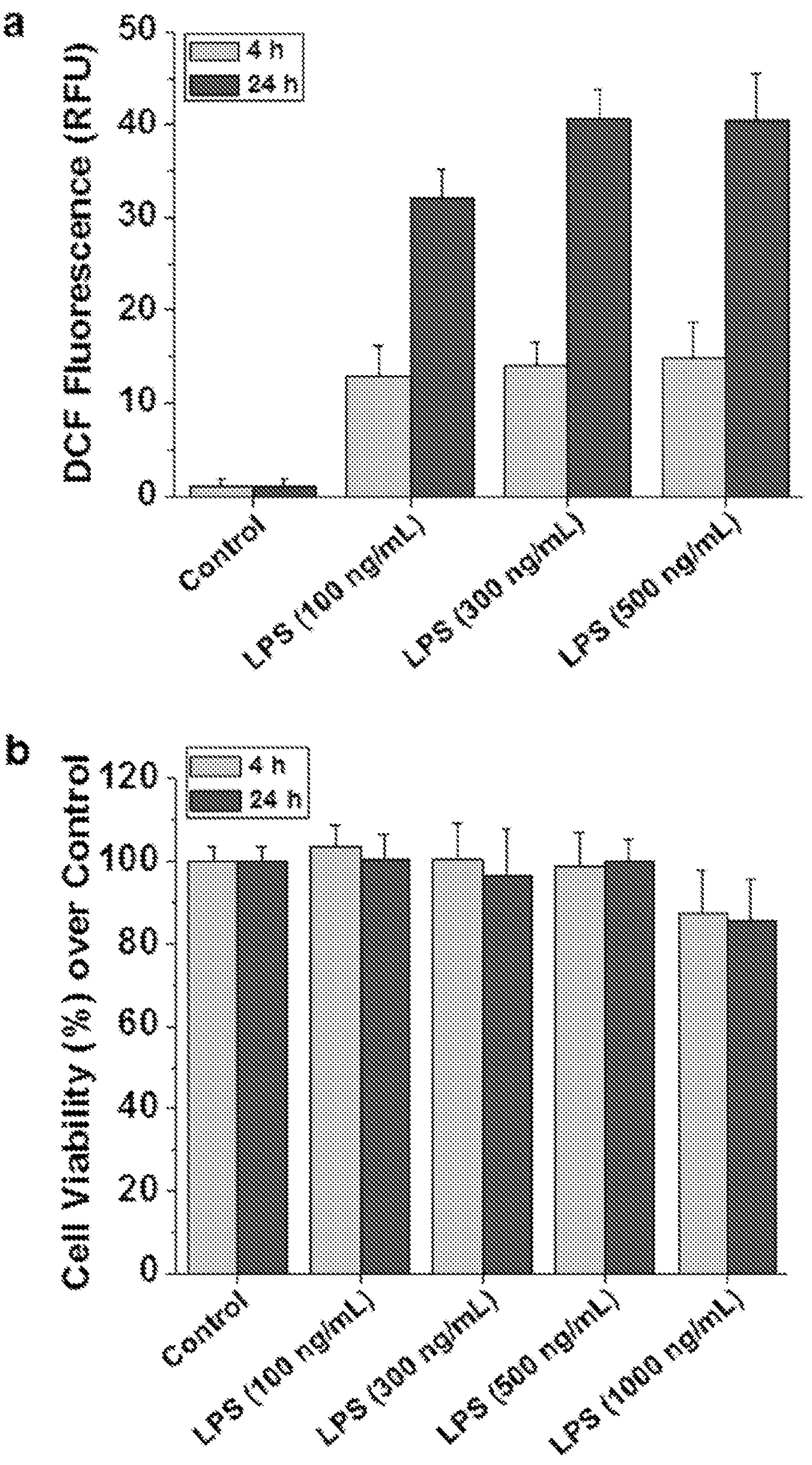
FIG. 8 shows reactive oxygen species (ROS) production and lipopolysaccharide (LPS) concentration.

To analyze the inhibitory effect of IL-10 on intracellular reactive oxygen species (ROS) generated from lipopolysaccharide (LPS)-stimulated macrophage cells, RAW 264.7 macrophage cells were seeded on a 24-well tissue culture plate at a density of $2\times10^4$ cells per well and then allowed to grow for 12 h. The cells were pre-treated with IL-10 at various concentrations (1 to 100 ng/mL) for 2 h and 24 h at 37° C. Then the medium was replaced with LPS solution (100 ng/mL), and the cells were further incubated for 4 h and 24 h at 37° C. The cells were then washed with PBS and incubated with 10 μM ROS detection reagent ($DCFH_2$-DA) for 90 min at 37° C. Fluorescence intensity was measured using a Synergy HT multi-mode microplate reader with ex/em 485/528 nm filter (BioTek Instruments Inc). In addition, the in vitro cytotoxicity of LPS was assessed by CCK-8 (cell counting kit-8, Dojindo Laboratories, Kumamoto, Japan) assay before the measurement of intracellular ROS, and showed no cytotoxicity, even up to 500 ng/mL LPS concentration (FIG. 8*b*).

In order to determine the bioactive integrity of IL-10 released from or loaded into TNPs, cells seeded on a 24-well tissue culture plate ($2\times10^4$ cells/well) were pre-treated with native IL-10, IL-10 released from TNPs (obtained at 48 h post-release), or IL-10-loaded TNPs at 50 ng/mL concentration for 24 h at 37° C. Next, the medium was replaced with LPS solution (100 ng/mL), and the cells were stimulated with LPS for 24 h at 37° C. After washing with PBS, intracellular ROS was measured using the detection method mentioned above. More importantly, the efficacy of post-treatment (LPS→IL-10 treatment) with IL-10 in stimulated macrophage cells was also assessed simply by reversing the order of sample addition used in pre-treatment with IL-10 (IL-10→LPS treatment). All measurements were performed in triplicate.

Figure 9:
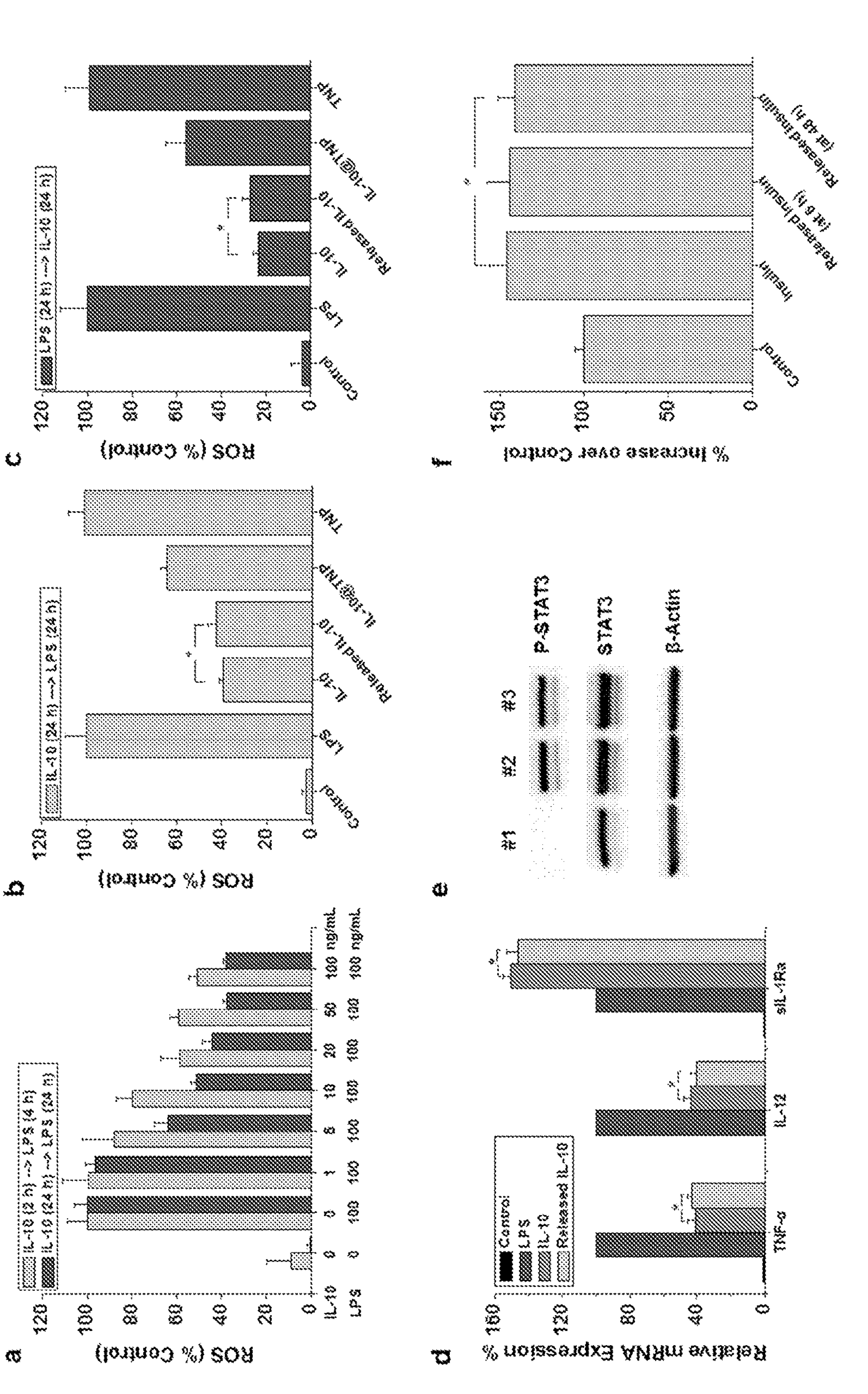
FIG. 9 shows the bioactivity of proteins released from TNPs.

The intracellular reactive oxygen species (ROS) generated from LPS-stimulated RAW 264.7 macrophages was measured with a widely used ROS detection kit ($DCFH_2$-DA).[1,2] Before the inhibitory effect of IL-10 on the ROS formation was checked, LPS treatment conditions for cell stimulation were optimized by varying the concentration of LPS (100, 300, and 500 ng/mL) and incubation time (4 and 24 h). Overproduction of ROS increased with stimulation time of LPS with macrophages,[3] whereas the LPS concentration (ranging from 100 ng/mL to 500 ng/mL) did not significantly affect ROS generation, implying that LPS with 100 ng/mL was enough to induce ROS (FIG. 8*a*). The inhibitory effect of IL-10 on ROS production in LPS-induced macrophages was investigated using various concentrations (1-100 ng/mL) of IL-10 and 100 ng/mL of LPS (FIG. 9*a*). The dose-dependent inhibition effect of IL-10 on ROS production was observed more clearly through the pre-treatment of cells with IL-10 for 24 h and stimulation with LPS for 24 h, compared to the shorter induction time of cells pre-treated with IL-10 and LPS[4].

To assess the biological integrity/activity of IL-10 released from nanoparticles, native IL-10, IL-10 released from nanoparticles at 48 h, and IL-10-loaded nanoparticles at 50 ng/mL of IL-10 and 100 ng/mL of LPS, were evaluated. In the case of pre-treatment of cells with IL-10 (i.e., the prophylactic concept), there was almost no statistical difference between the released IL-10 and native IL-10 ($^{\#}p>0.05$) (FIG. 9*b*). Interestingly, in the case of IL-10-loaded nanoparticles, lower activity indicated that IL-10 was still inside the nanoparticles, suggesting both efficient loading and controlled release. More importantly, in the case of post-treatment of cells with IL-10 (i.e., the therapeutic concept), the inhibitory effect on ROS production was enhanced with all samples; most notably, the bioactivity of released IL-10 was similar to that of the native protein (FIG. 9*c*), indicating that it was maintained during both loading and release.

Example 5

Bioactivity Analysis of IL-10 Using qPCR and Western Blot

Quantitative Real-Time PCR (qPCR)

Macrophage cells were seeded on a 6-well tissue culture plate (5×10$^5$ cells/well) and maintained for 12 h. The cells were treated with LPS (500 ng/mL) for 4 h, the medium was replaced with IL-10 solution (native IL-10 or released IL-10 at 20 ng/mL), and the cells were incubated for 2 h at 37° C. Next, the cells were washed with PBS and harvested by scraping, followed by centrifugation at 2,000 rpm for 5 min at 4° C. The isolated cell pellets were used to prepare the total RNA using the RNeasy® Mini Kit (QIAGEN, Valencia, Calif., USA) according to the manufacturer's protocol. For the preparation of cDNA, the extracted RNA solution (1 μg/5 μL) was then mixed with 0.5 μL of Oligo (dT) 15 primer (Promega, Madison, Wis., USA) and then reacted at 70° C. for 5 min using the Bio-Rad iCycler PCR Thermal Cycler (Bio-Rad Laboratories, Inc., Hercules, Calif., USA). The mixture was subsequently placed on ice for 5 min and mixed with various components to a final volume of 20 μL: nuclease-free water (5.6 μL), 10 mM dNTP mixture (Promega, 1 μL), 25 mM $MgCl_2$ (Promega, 2.4 μL), ImProm-II™ reverse transcriptase (Promega, 1 μL), ImProm-II™ 5× reaction buffer (Promega, 4 μL), and RNasin® Plus RNase inhibitor (Promega, 0.5 μL). Next, the mixture was subjected to Bio-Rad iCycler PCR Thermal Cycler in three steps: 5 min at 25° C., 60 min at 42° C., and 15 min at 70° C. To analyze the gene expression of proinflammatory cytokines affected by IL-10 in LPS-stimulated macrophage cells, the synthesized cDNA was mixed with the Rotor-Gene® SYBR® Green PCR Kit (QIAGEN) as a fluorescent reporter and then the primer mixture containing TNF-α (SEQ ID No. 1: 5'-CCACCACGCTCTTCTGTCTA-3' and SEQ ID No. 2: 5'-AGGGTCTGGGCCATAGAACT-3'), IL-12 (SEQ ID No. 3: 5'-GAACTTGTCAAAGGCTTCATCTGCAAGTTC-3' and SEQ ID No. 4: 5'-GGAAGCACGGCAGCAGAATA-3'), sIL-1Ra (SEQ ID No. 5: 5'-AAATCTGCTGGGGACCCTAC-3' and SEQ ID No. 6: 5'-TCCCAGATTCTGAAGGCTTG-3') or β-Actin (SEQ ID No. 7: 5'-CGGTTCCGATGCCCTGAGGCTCTT-3' and SEQ ID No. 8: 5'-CGTCACACTTCATGATGGAATTGA-3') primer pairs, respectively. Next, the final reaction mixture was subjected to qPCR cycling (Rotor-Gene Q, QIAGEN), and the amplification reactions were carried out using the following protocol. After an initial denaturation at 95° C. for 5 min, the cycles processed to denaturation at 95° C. for 10 seconds, and annealing and elongation at 60° C. for 20 seconds were performed 40 times. The relative gene expression levels were calculated using the ΔΔCt method and normalized to the expression of the reference gene (β-Actin). The threshold cycle (Ct) values of the target genes were also normalized to the values of unstimulated cells (control group). The measurements were carried out in triplicate.

Western Blot Analysis

To determine the bioactivity of IL-10 in unstimulated cells, macrophage cells seeded on a 6-well tissue culture plate (5×10$^5$ cells/well) were treated with IL-10 (native IL-10 or released IL-10 at 20 ng/mL) and incubated for 24 h at 37° C. Then the cells were washed with ice-cold PBS three times and harvested by scraping into Eppendorf tubes, followed by centrifugation at 12,000 rpm for 5 min at 4° C. For protein extraction, the cells were lysed in 200 μL of protein extraction reagent (Fisher Scientific, Pittsburgh, Pa., USA) supplemented with protease inhibitor cocktail and phosphatase inhibitor cocktail (Sigma-Aldrich), and then centrifuged at 12,000 rpm for 10 min at 4° C. to remove the nuclei. Next, protein concentration was measured using a Coomassie Plus-Bradford™ assay with bovine serum albumin as the protein standard. The cell lysates (with 30 μg of protein) were mixed with 4× Laemmli Sample Buffer (Bio-Rad), and the mixture was boiled for 7 min at 95° C. The proteins were separated by SDS-PAGE using Novex® 4-12% Tris-Glycine Mini Gels and subsequently electro-transferred onto an Immobilon-P polyvinylidene difluoride (PVDF) membrane (Millipore). Then the membranes were blocked with Tris-Buffered Saline-0.1% Tween 20 (TBST) solution containing 5% BSA for 2 h at 4° C. on a shaker. The primary antibodies (1:1000 dilutions) in TBST with 3% BSA were incubated with the membranes overnight at 4° C. on a shaker. After that, the membranes were washed with TBST solution four times (each 10 min) and then incubated with secondary antibody (1:10,000 dilutions) in TBST with 3% BSA for 1 h at room temperature on a shaker. Finally, the membranes were washed with TBST solution five times and visualized using Amersham ECL prime western blotting detection reagent (GE Healthcare Life Sciences, Pittsburgh, Pa., USA). The primary and secondary antibodies used in this study were from Cell Signaling Technology (Danvers, Mass., USA) as follows: β-Actin (8H10D10) Mouse mAb, Stat3 (124H6) Mouse mAb, and Phospho-Stat3 (Tyr705) (3E2) Mouse mAb as a primary antibody, and anti-mouse IgG (HRP-linked) antibody as a secondary antibody.

The relative gene expression levels of TNF-α and IL-12 were compared with the native IL-10 through qPCR (FIG. 9*d*). Expression was dramatically increased after LPS stimulation, and then the released IL-10 reduced the expression of cytokines (ca. 2.5-fold), suggesting that the released IL-10 not only retains bioactivity, but also functions as an anti-inflammatory cytokine, with results similar to native IL-10. In addition, IL-10 treatment increased sIL-1Ra promoter activity by 1.5-fold compared to LPS alone, and the released IL-10 had effects identical to those of the native protein, consistent with the unique response of IL-10 to the gene expression of the secretory interleukin-1 (IL-1) receptor antagonist (sIL-1Ra), for which previous studies demonstrate the potential to treat metastatic cancers[5]. The gene expression of several cytokines analyzed in this study suggests that the bioactivity of IL-10 released from the nanoparticles was successfully maintained inside the hydrophilic shell.

Western blots were also employed to determine the bioactivity of released IL-10. Since IL-10 has been known to signal via the activation of the signal transducer and activator of transcription 3 (STAT3), which is a key mediator of the inflammatory response of macrophages and other immune cell types[6], the levels of STAT3 and phosphorylated STAT3 (P-STAT3 at Tyr705) were measured. Compared to the control group, the total levels of STAT3 were slightly increased by IL-10 treatment, using β-Actin as a reference protein (FIG. 9*e*). Moreover, the clear band of P-STAT3 was observed in the native IL-10 group, indicating the activation of STAT3 by IL-10 treatment. The levels of STAT3 and P-STAT3 in the native IL-10 and released IL-10 groups (respectively) were almost identical, suggesting that IL-10 maintained biological integrity throughout the loading process and after release.

Example 6

Bioactivity Analysis of Insulin Using MCF-7 Cells

Insulin-Dependent Proliferation Effect of MCF-7.

MCF-7 human breast cancer cells were seeded on a 24-well tissue culture plate at a density of $2\times10^4$ cells per well and allowed to grow for 12 h. Then the cells were washed with PBS and incubated with serum-free medium (SFM) for 24 h. Next, native insulin (1~500 nM) and insulin (10 nM) released from TNPs at 6 h and 48 h were added to the cells and incubated for another 24 h. The effects of insulin on the cells were assessed using the CCK-8 assay (cell counting kit-8, Dojindo Laboratories, Kumamoto, Japan). Briefly, the medium was replaced with fresh SFM containing 10×-diluted CCK-8. After 1 h incubation in the dark, the absorbance of the colored medium was measured at 450 nm using a Synergy HT multi-mode microplate reader.

For all comparisons, statistical analysis was carried out using the Student t test, and the minimal level of significance was $p<0.05$.

Figure 10:
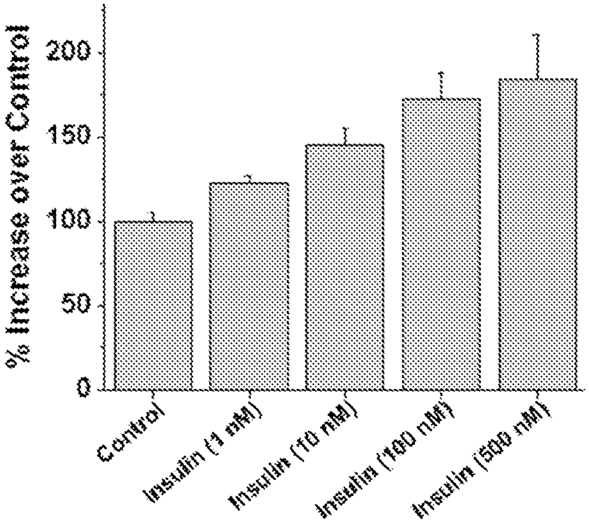
FIG. 10 shows insulin dose-dependent cell proliferation. Enhanced proliferation effect of MCF-7 by insulin at various concentrations (1-500 nM). Insulin-dependent proliferation of MCF-7 was compared to the control (no insulin) and analyzed by CCK-8 assay (n=3).

The bioactivity of insulin released from TNPs was analyzed via insulin-dependent proliferation of MCF-7, as reported previously'. It was confirmed that the proliferation of MCF-7 cells was insulin dose-dependent from 1 to 500 nM (FIG. 10). The enhancement in cell growth (over the control group) produced by native insulin and released insulin (6 h and 48 h post-release) at 10 nM concentration in serum-free medium were compared (FIG. 9*f*). The released insulin produced almost the same increase in cellular metabolic activity as native insulin (no statistical differences, $p>0.05$).

Example 7

Pharmacokinetics of Protein-Loaded TNPs

In Vivo Animal Test.

All animal experiments were handled under the guidelines of the Animal Care and Use Committee of Harvard Medical School. Wild-type Balb/c mice (20 g) and C57BL/6 mice (6-8 weeks old) were purchased from Charles River Laboratories International, Inc. (Wilmington, Mass., USA).

Pharmacokinetic Analysis.

Wild-type Balb/c mice were administered a single intravenous (i.v.) dose of IL-10, IL-10 loaded TNPs (100 μg IL-10/kg), insulin, or insulin-loaded TNPs (1 U Insulin/kg) diluted in 0.85% saline solution through the tail vein. At 5 min, 30 min, 1 h, 2 h, 4 h, 8 h, 12 h, and 24 h post-injection, blood samples (0.5 mL) were drawn for serum protein concentration analysis. Next, the blood samples were placed at 4° C. overnight to allow the formation of a blood clot and centrifuged under 2,000×g for 15 min at 4° C. The serum samples were stored at −80° C. and analyzed using an ELISA kit. Finally, the pharmacokinetic parameters were calculated using a noncompartmental model for both IL-10 and insulin[8,9]. The AUC (area under the serum concentration-time curve) and AUMC (area under the first moment curve) were calculated using the trapezoidal rule. The total body clearance (Clearance), mean residence time (MRT), volume of distribution at steady state (Vss), and terminal half-life ($T_{1/2}$ terminal) were calculated as follows: Clearance=Dose/AUC, MRT=AUMC/AUC, Vss=Clearance×MRT, $T_{1/2}$ terminal=LN(2)/kel' (kel' (apparent elimination rate constant)=1/MRT).

Figure 11:
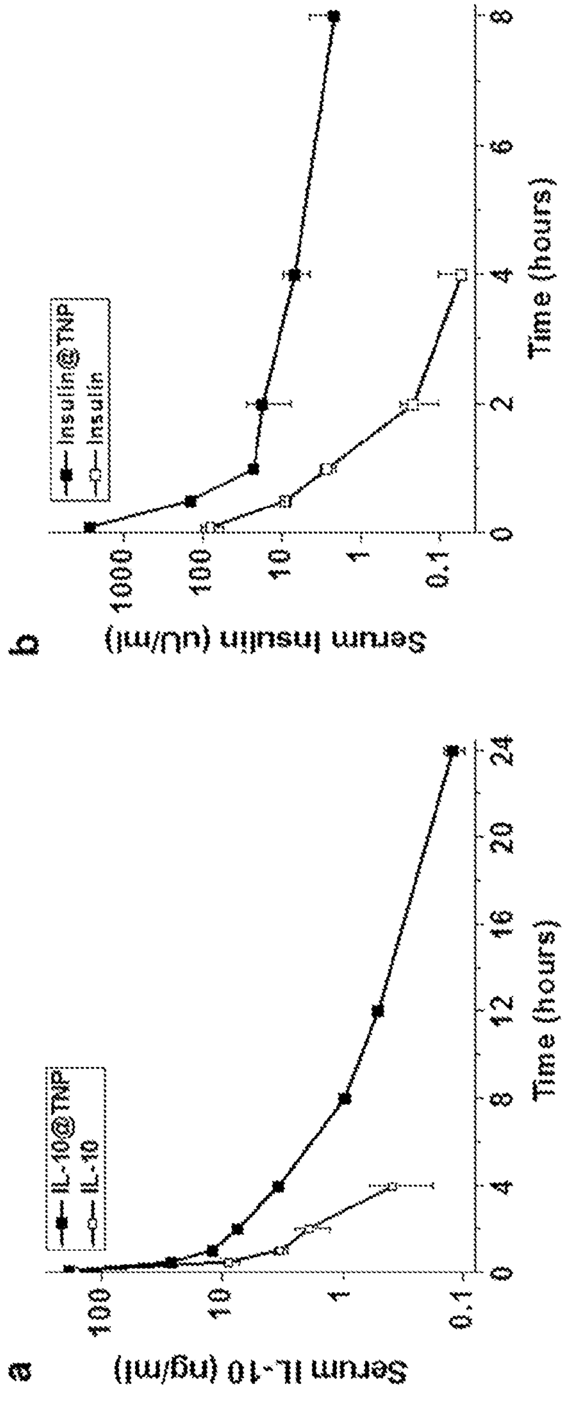
FIG. 11 shows pharmacokinetics of protein-loaded TNPs. Changes in serum protein levels in mice after intravenous administration of IL-10 and IL-10-loaded TNP (FIG. 11*a*), and insulin and insulin-loaded TNP (FIG. 11*b*). The serum concentrations of proteins were measured at several time points using ELISA kits (mean±SEM, n=3).

Protein-loaded TNPs [IL-10@TNPs (100 μg IL-10/kg) and Insulin@TNPs (1 U Insulin/kg)] were administered intravenously to mice, and blood samples were collected at different time points to analyze the serum concentration of proteins (FIG. 11). The mean pharmacokinetic parameters of the proteins were assessed by noncompartmental analysis (Table 1). After intravenous administration of IL-10 alone, the serum IL-10 concentration rapidly decreased until the 8-hr point, whereas the concentration was maintained up to 24 hr when using TNPs (FIG. 11*a*), increasing the area under the serum concentration-time curve (AUC) 1.9-fold (from 50.52 to 97.73 ng·hr/ml) (Table 1). In addition, IL-10-loaded TNPs reduced the clearance 1.9-fold (from 1979.57 to 1023.18 $ml\cdot hr^{-1}\cdot kg^{-1}$) and improved the half-life 5.9-fold (from 0.25 to 1.48 hr) compared with IL-10 alone. Similar results were obtained when insulin-loaded TNPs were injected into mice (FIG. 11*b*). The insulin-loaded TNPs produced a remarkable increase in systemic exposure (30.9-fold, from 25.97 to 804.99 μU·hr/ml) compared with the insulin-alone group (Table 1). The group using TNPs also showed significantly reduced clearance (31-fold) and prolonged half-life of insulin (1.6-fold).

TABLE 1

Pharmacokinetic parameters. Pharmacokinetic parameters of IL-10, IL-10-loaded TNP, insulin, and insulin-loaded TNP administered intravenously to mice. The parameters were analyzed using a noncompartmental model. AUC, area under the concentration-time curve; Vss, volume of distribution at steady state; MRT, mean residence time.

| Parameter | IL-10 | IL-10@TNP | Insulin | Insulin@TNP |
|---|---|---|---|---|
| Dose | 100 μg/kg | 100 μg/kg | 1 U/kg | 1 U/kg |
| Clearance ($ml \cdot hr^{-1} \cdot kg^{-1}$) | 1979.57 | 1023.18 | 38512.48 | 1242.25 |
| Vss (ml/kg) | 707.27 | 2179.42 | 10159.47 | 531.18 |
| $AUC_{0-\infty}$ | 50.52 ng · hr/ml | 97.73 ng · hr/ml | 25.97 μU · hr/ml | 804.99 μU · hr/ml |
| MRT (hr) | 0.36 | 2.13 | 0.26 | 0.43 |
| $T_{1/2}$ terminal (hr) | 0.25 | 1.48 | 0.18 | 0.30 |

Example 8

In Vivo Efficacy of Protein-Loaded TNPs

In Vivo Efficacy on Allergic Contact Dermatitis (ACD).

DNFB Treatment and Ear Measurement.

C57BL/6 mice were administered i.v. saline, TNPs, IL-10, or IL-10-loaded TNPs (100 μg IL-10/kg). At 2 h post-injection, a 0.3% v/v solution of DNFB (2,4-dinitro-fluorobenzene) in acetone was applied the mice to the dorsal and ventral aspects of ear skin. Ear thickness was measured using an engineer's micrometer (Mitutoyo) at 36 h. The change of ear thickness is calculated as the difference between the treated ear and the contralateral ear treated with acetone alone.

Histology.

Ears were fixed in a 10% formalin solution, embedded in paraffin, and submitted for histological analysis by haematoxilin and eosin staining to the Harvard Rodent Histopathology Core.

Tissue Digestion and Flow Cytometry.

For ear-skin digestion, the dorsal and ventral aspects of the ear were mechanically separated before mincing and placing into a digestion mix consisting of DMEM (Gibco) supplemented with HEPES (Invitrogen), 2% FCS, 200 μg/mL Liberase TM (Roche), 10 μg/mL DNase I (Roche), and 5 mg/mL Collagenase D (Roche). Ears were digested for 80 minutes at 37° C. in gentleMACS tubes (Miltenyi) with gentle agitation in freshly prepared digestion mix. After enzymatic digestion, the mixture was processed using a gentleMACS homogenizer (Miltenyi) in order to obtain a cell suspension, which was then filtered through a 70 μm cell strainer (BD). Cells were then resuspended in FACS buffer for analysis.

Single-cell suspensions in FACS Buffer (PBS with 2 mM EDTA and 2% FCS (Invitrogen-GIBCO) were pre-incubated with Fc-Block (clone 2.4G2). Then cell suspensions were incubated with the following antibodies: FITC-conjugated anti-Ly-6G (Clone 1A8; BD Pharmingen), PE-conjugated anti-Ly-6C (Clone HK1.4; Biolegend), PerCP/Cy5.5-conjugated anti-CD45.2 (Clone 104; Biolegend), PE-Cy7-conjugated anti-CD11c (Clone HL3; BD Pharmingen), Alexa647-conjugated anti-CD11b (Clone M1/70; Biolegend), and APC-Cy7-conjugated anti-I-A/I-E "Class-II" (Clone M5/114.15.2; Biolegend). Cells were then washed with PBS and resuspended in MACS buffer for immediate acquisition.

For analysis, cells were acquired on a BD FACS CANTO (BD Pharmingen) and analyzed using FlowJo software (Treestar Inc.).

The statistical significance of differences among the groups was calculated with a one-way ANOVA followed by Dunnett's post-tests as well as the Student t test. Here the minimal level of significance was set at $p<0.05$.

Figure 12:
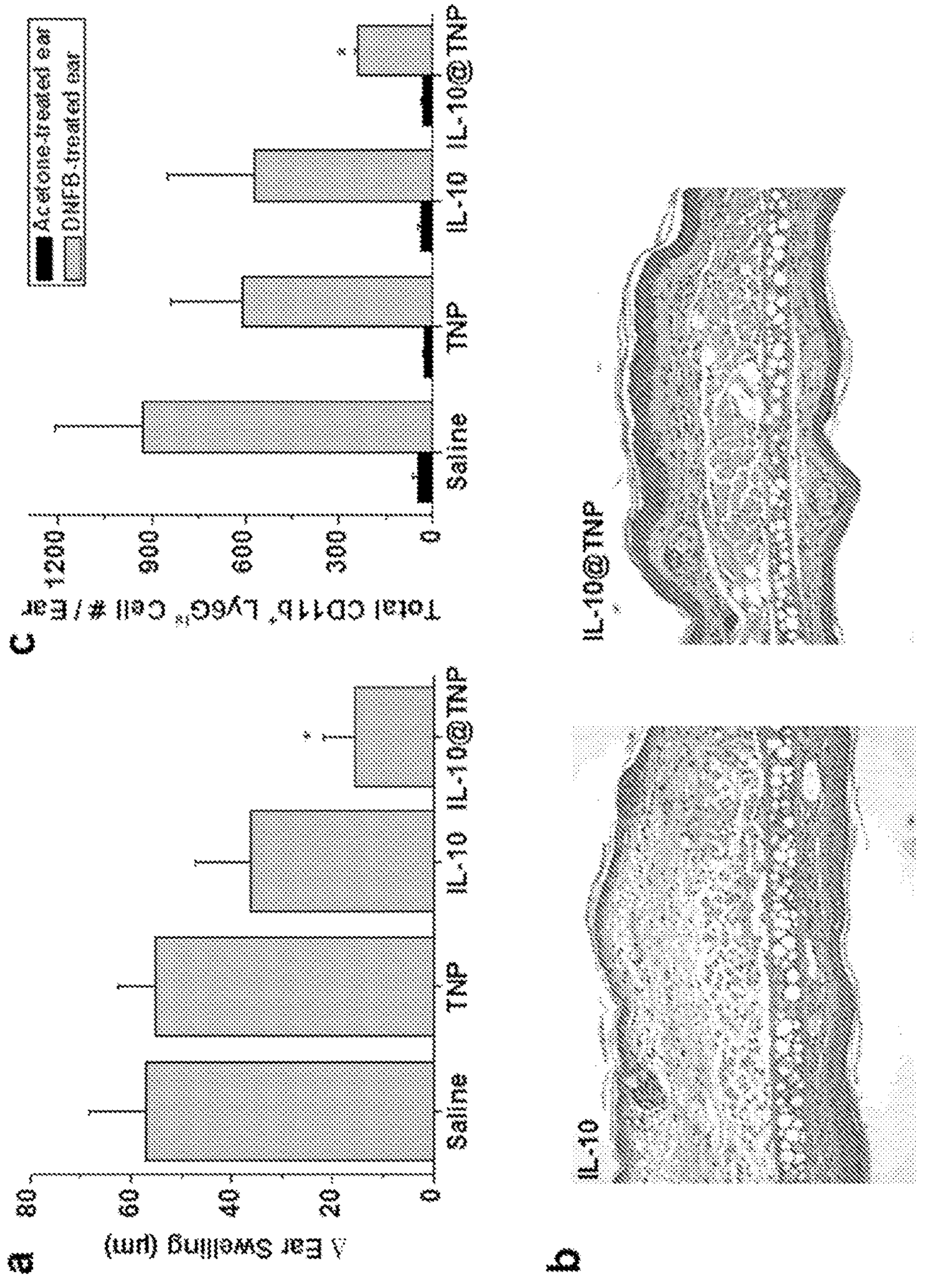
FIG. 12 shows in vivo anti-inflammatory efficacy of IL-10-loaded TNPs.

In order to determine whether TNPs are an efficient delivery platform for protein drugs in vivo, mice were treated systemically with saline, TNPs, IL-10 (100 Kg/kg), or IL-10-loaded TNPs (100 μg IL-10/kg). At 2 h post-injection, DNFB was then applied topically to the dorsal and ventral aspects of ear skin, and the ensuing inflammatory response was assessed based on the change in ear swelling and the number of the myeloid cells that infiltrated the ear tissue (FIG. 12).

IL-10 has been reported to be able to reduce inflammation in DNFB-induced allergic contact dermatitis (ACD)[10]. As shown in FIG. 12*a*, although the administration of IL-10 resulted in a reduction of ear swelling compared to the saline-treated control, IL-10-loaded TNPs (IL-10@TNPs) reduced ear swelling much more than IL-10 alone. In addition, mice treated with IL-10@TNPs had less edema and myeloid infiltration than mice injected with IL-10 alone (FIG. 12*b*) and showed greater reduction of neutrophil numbers than the saline group (FIG. 12*c*). The TNPs alone did not elicit any anti-inflammatory effect, indicating that the anti-inflammatory actions of IL-10@TNPs was due to IL-10, not the polymeric composition of the TNPs.

Herein is shown a nanoparticle platform with a simple solvent-free encapsulation method and efficient loading content for effective delivery of various labile therapeutic proteins, with a potentially significant beneficial impact on protein delivery. TNPs can deliver proteins without organic solvents, helping to retain bioactivity. The TNPs also showed strong structural stability in a model serum buffer and in resuspension conditions without the need for any cryo-protectants, suggesting that this platform would be amenable to clinical translation. Based on the results of ROS, qPCR, western blot, and protein-dependent cell proliferation assay in vitro, the bioactivity of proteins (e.g., IL-10, insulin) appeared well preserved inside nanoparticles. More importantly, the TNPs significantly increased the half-life and systemic exposure of model therapeutic proteins such as IL-10 ($t_{1/2}$ 5.9-fold) and insulin ($t_{1/2}$ 1.6-fold) in mice without chemical modifications. Hence, TNPs as a general solvent-free delivery nano-platform for the efficient delivery of many other therapeutic proteins offers significant clinical potential.

REFERENCES

1. Chang, L. P., Lai, Y. S., Wu, C. J. & Chou, T. C. Liquid perfluorochemical inhibits inducible nitric oxide synthase expression and nitric oxide formation in lipopolysaccharide-treated RAW 264.7 macrophages. *J. Pharmacol. Sci.* 111, 147-154 (2009).
2. Hernandez-Ledesma, B., Hsieh, C. C. & de Lumen, B. O. Antioxidant and anti-inflammatory properties of cancer preventive peptide lunasin in RAW 264.7 macrophages. *Biochem. Biophys. Res. Commun.* 390, 803-808 (2009).
3. Kim, J. Y., Choi, W. I., Kim, Y. H. & Tae, G. Highly selective in-vivo imaging of tumor as an inflammation site by ROS detection using hydrocyanine-conjugated, functional nano-carriers. *J. Control. Release* 156, 398-405 (2011).

4. Dokka, S. et al. Interleukin-10-mediated inhibition of free radical generation in macrophages. *Am. J. Physiol. Lung Cell Mol. Physiol.* 280, L1196-L1202 (2001).

5. Carl, V. S., Gautam, J. K., Comeau, L. D. & Smith, M. F. Jr. Role of endogenous IL-10 in LPS-induced STAT3 activation and IL-1 receptor antagonist gene expression. *J. Leukoc. Biol.* 76, 735-742 (2004).

6. Capiralla, H. et al. Identification of potent small-molecule inhibitors of STAT3 with anti-inflammatory properties in RAW 264.7 macrophages. *FEBS J.* 279, 3791-3799 (2012).

7. Chappell, J. et al. Effect of insulin on cell cycle progression in MCF-7 breast cancer cells. Direct and potentiating influence. *J. Biol. Chem.* 276, 38023-38028 (2001).

8. Huhn, R. D. et al. Pharmacokinetics and immunomodulatory properties of intravenously administered recombinant human interleukin-10 in healthy volunteers. *Blood* 87, 699-705 (1996).

9. Hinds, K. D. & Kim, S. W. Effects of PEG conjugation on insulin properties. *Adv. Drug Deliv. Rev.* 54, 505-530 (2002).

10. Schwarz, A. et al. In vivo effects of interleukin-10 on contact hypersensitivity and delayed-type hypersensitivity reactions. *J. Invest. Dermatol.* 103, 211-216 (1994).

11. Tabas, I. & Glass, C. K. Anti-inflammatory therapy in chronic disease: challenges and opportunities. *Science* 339, 166-172 (2013).

Other Embodiments

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

What is claimed is:

1. A composition comprising:

a nanoparticle comprising a core and an outer layer comprising a polymer surrounding the core; and a biomolecule selectively encapsulated in the outer layer of the nanoparticle;

wherein the polymer exhibits temperature-dependent conformational changes that change the size of the nanoparticle by an amount sufficient to provide for encapsulation of the biomolecule from an aqueous medium substantially free of organic solvent, wherein the composition is prepared by a method comprising:

(a) preparing a composition comprising the nanoparticle comprising the core and the outer layer comprising the polymer surrounding the core; an aqueous medium substantially free of organic solvent; and the biomolecule dissolved or suspended in the aqueous medium;

(b) subjecting the composition to a first temperature at which the polymer expands to allow entry of the biomolecule into the outer layer; and (c) subjecting the composition to a second temperature at which the polymer contracts to encapsulate the biomolecule in the outer layer; and wherein the polymer surrounding the core is not cross-linked.

2. The composition of claim 1, wherein the amount sufficient to provide for encapsulation of the biomolecule from an aqueous medium substantially free of organic solvent is in the range of about 5% to about 500%.

3. The composition of claim 1, wherein the core comprises an aliphatic polyester polymer selected from the group consisting of: a polylactic acid, a polyglycolic acid, and a copolymer of lactic acid and glycolic acid.

4. The composition of claim 1, wherein the outer layer comprises a poloxamer having the formula:

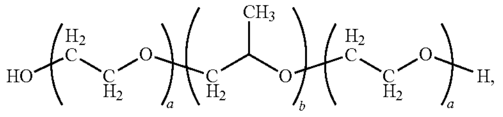

wherein a is an integer in the range of about 2 to about 200 and b is an integer in the range of about 10 to about 100.

5. The composition of claim 4, wherein the poloxamer polymer comprises a poly(propylene oxide) central chain in a range from about 3000 g/mol to about 5000 g/mol.

6. The composition of claim 4, wherein the poloxamer polymer comprises a poly(ethylene oxide) content in a range from about 60% to about 80% by weight.

7. The composition of claim 1, wherein the biomolecule is erythropoietin, insulin, human growth hormone, interleukin-2 or interleukin-10.

8. The composition of claim 1, wherein:

the core comprises an aliphatic polyester polymer selected from the group consisting of: a polylactic acid, a polyglycolic acid, and a copolymer of lactic acid and glycolic acid; and the outer layer comprises a poloxamer having the formula:

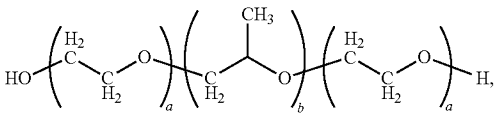

wherein a is an integer in the range of about 2 to about 200 and b is an integer in the range of about 10 to about 100.

9. The composition of claim 1, wherein the first temperature is in the range of about 0° C. to about 20° C., and the second temperature is in the range of about 20° C. to about 50° C.

10. A method of delivering a therapeutic biomolecule to a subject in need thereof, the method comprising administering to the subject in need thereof a therapeutically effective amount of a composition of claim 1.

11. The method of claim 10, wherein the therapeutic biomolecule is selected from the group consisting of: erythropoietin, insulin, human growth hormone, interleukin-2 and interleukin-10.

* * * * *

UNITED STATES PATENT AND TRADEMARK OFFICE

CERTIFICATE OF CORRECTION

PATENT NO. : 10,272,050 B2
APPLICATION NO. : 15/519052
DATED : April 30, 2019
INVENTOR(S) : Omid C. Farokhzad et al.

It is certified that error appears in the above-identified patent and that said Letters Patent is hereby corrected as shown below:

On the Title Page

Column 2 item (74) (Attorney, Agent or Firm), Line 2, delete “Vasity” and insert -- Vasily --

Signed and Sealed this
Sixth Day of August, 2019

Andrei Iancu
*Director of the United States Patent and Trademark Office*

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: laboratory-synthesized primer

<400> SEQUENCE: 1

ccaccacgct cttctgtcta                                        20


<210> SEQ ID NO 2
<211> LENGTH: 20
<212> TYPE: DNA
<213> ORGANISM: Artificial Sequence
<220> FEATURE:
<223> OTHER INFORMATION: laboratory-synthesized primer

<400> SEQUENCE: 2

agggtctggg ccatagaact                                        20


<210> SEQ ID NO 3
<211> LENGTH: 30
<212> TYPE: DNA
<213> ORGANISM: Artificial Sequence
<220> FEATURE:
<223> OTHER INFORMATION: laboratory-synthesized primer

<400> SEQUENCE: 3

gaacttgtca aaggcttcat ctgcaagttc                             30


<210> SEQ ID NO 4
<211> LENGTH: 20
<212> TYPE: DNA
<213> ORGANISM: Artificial Sequence
<220> FEATURE:
<223> OTHER INFORMATION: laboratory-synthesized primer

<400> SEQUENCE: 4

ggaagcacgg cagcagaata                                        20
```

-continued

```
<210> SEQ ID NO 5
<211> LENGTH: 20
<212> TYPE: DNA
<213> ORGANISM: Artificial Sequence
<220> FEATURE:
<223> OTHER INFORMATION: laboratory-synthesized primer

<400> SEQUENCE: 5

aaatctgctg gggaccctac                                                  20


<210> SEQ ID NO 6
<211> LENGTH: 20
<212> TYPE: DNA
<213> ORGANISM: Artificial Sequence
<220> FEATURE:
<223> OTHER INFORMATION: laboratory-synthesized primer

<400> SEQUENCE: 6

tcccagattc tgaaggcttg                                                  20


<210> SEQ ID NO 7
<211> LENGTH: 24
<212> TYPE: DNA
<213> ORGANISM: Artificial Sequence
<220> FEATURE:
<223> OTHER INFORMATION: laboratory-synthesized primer

<400> SEQUENCE: 7

cggttccgat gccctgaggc tctt                                             24


<210> SEQ ID NO 8
<211> LENGTH: 24
<212> TYPE: DNA
<213> ORGANISM: Artificial Sequence
<220> FEATURE:
<223> OTHER INFORMATION: laboratory-synthesized primer

<400> SEQUENCE: 8

cgtcacactt catgatggaa ttga                                             24
```